United States Patent
Venkataraman et al.

(10) Patent No.: US 6,597,996 B1
(45) Date of Patent: Jul. 22, 2003

(54) METHOD FOR INDENTIFYING OR CHARACTERIZING PROPERTIES OF POLYMERIC UNITS

(75) Inventors: Ganesh Venkataraman, Woburn, MA (US); Zachary Shriver, Cambridge, MA (US); Rahul Raman, Cambridge, MA (US); Ram Sasisekharan, Cambridge, MA (US); Nishla Keiser, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/558,137

(22) Filed: Apr. 24, 2000

Related U.S. Application Data

(60) Provisional application No. 60/159,940, filed on Oct. 14, 1999, provisional application No. 60/159,939, filed on Oct. 14, 1999, provisional application No. 60/130,792, filed on Apr. 23, 1999, and provisional application No. 60/130,747, filed on Apr. 23, 1999.

(51) Int. Cl.[7] ............................................. G06F 19/00
(52) U.S. Cl. ......................................................... 702/27
(58) Field of Search ........................... 702/27; 424/484; 250/288, 282; 435/6, 69.1, 91.1, 23; 264/177, 184; 535/26; 521/25

(56) References Cited

U.S. PATENT DOCUMENTS

| | | | |
|---|---|---|---|
| 4,281,108 A | 7/1981 | Fussi | 536/21 |
| 4,341,869 A | 7/1982 | Langer, Jr. et al. | 435/232 |
| 4,373,023 A | 2/1983 | Langer et al. | 435/2 |
| 4,396,762 A | 8/1983 | Langer et al. | 536/21 |
| 4,443,545 A | 4/1984 | Langer, Jr. et al. | 435/232 |
| 4,551,296 A * | 11/1985 | Kavensh et al. | 264/177 |
| 4,745,105 A | 5/1988 | Griffin et al. | 514/56 |
| 4,757,056 A | 7/1988 | Van Gorp et al. | 514/54 |

(List continued on next page.)

FOREIGN PATENT DOCUMENTS

| | | | |
|---|---|---|---|
| EP | 0 433 225 A1 | 6/1991 | ............ C07K/7/10 |
| EP | 0 557 887 A2 | 9/1993 | ............ C08B/37/10 |
| WO | WO 93/08289 | 4/1993 | ............ C12N/15/60 |
| WO | WO 93/19096 | 9/1993 | ............ C08B/37/10 |
| WO | WO 94/21689 | 9/1994 | ............ C08B/37/10 |
| WO | WO 95/34635 | 12/1995 | ............ C12N/1/21 |
| WO | PCT/US96/17310 | 10/1996 | |
| WO | WO 97/16556 | 5/1997 | ............ C12N/15/60 |
| WO | PCT/US99/19841 | 1/2000 | |

OTHER PUBLICATIONS

Biemann K, Four decades of structure determination by mass spectrometry: from alkaloids to heparin. *J Am Soc Mass Spectrom* 2002; 13(11):1254–1272.

Rhomberg A et al., Mass spectrometric sequencing of heparin and heparin sulfate using partial digestion with heparinases, Proc. 45th Annual Conference on Mass Spectrometry Allied Topics, Jun. 1–5, 1997, Palm Springs, CA, p. 1026 (Abstract only).

Rhomberg AJ, Mass spectrometric and capillary electrophoretic investigation of heparin, heparinases and related compounds. Ph.D. thesis, MIT (Department of Chemistry), May 22, 1998.

Venkataraman G et al., Sequencing complex polysaccharides. *Science* Oct. 15, 1999; 286:537–542.

(List continued on next page.)

*Primary Examiner*—John Barlow
*Assistant Examiner*—Tung S Lau
(74) *Attorney, Agent, or Firm*—Wolf, Greenfield & Sacks PC

(57) ABSTRACT

The invention relates to methods of identifying and characterizing properties of polymers to provide information about the polymer such as the charge of the polymer, the number and types or characteristics of units of the polymer and the sequence of the polymers. The invention also relates to methods of sequencing polymers such as nucleic acids, polypeptides and polysaccharides and methods for identifying a polysaccharide-protein interaction.

9 Claims, 13 Drawing Sheets

U.S. PATENT DOCUMENTS

| | | | |
|---|---|---|---|
| 4,942,156 A | 7/1990 | Foley et al. .................. | 514/56 |
| 4,990,502 A | 2/1991 | Lormeau et al. .............. | 514/56 |
| 5,010,063 A | 4/1991 | Piani et al. ................... | 514/56 |
| 5,039,529 A | 8/1991 | Bergendal et al. .......... | 424/630 |
| 5,106,734 A | 4/1992 | Nielsen ....................... | 435/84 |
| 5,152,784 A | 10/1992 | Tsilibary ...................... | 623/1 |
| 5,164,378 A | 11/1992 | Conti et al. .................. | 514/56 |
| 5,169,772 A | 12/1992 | Zimmermann et al. ..... | 435/232 |
| 5,204,323 A | 4/1993 | Findlay et al. ............... | 514/2 |
| 5,252,339 A | 10/1993 | Cristofori et al. ........... | 424/479 |
| 5,262,325 A | 11/1993 | Zimmermann et al. ..... | 435/269 |
| 5,290,695 A | 3/1994 | Morikawa et al. .......... | 435/232 |
| 5,338,677 A | 8/1994 | Zimmermann et al. ..... | 435/200 |
| 5,389,539 A | 2/1995 | Sasisekharan et al. ...... | 435/220 |
| 5,474,987 A | 12/1995 | Cohen et al. ................. | 514/56 |
| 5,567,417 A | 10/1996 | Sasisekharan et al. ..... | 424/94.5 |
| 5,569,600 A | 10/1996 | Sasisekharan et al. ...... | 435/220 |
| 5,576,304 A | 11/1996 | Kakkar et al. ................ | 514/56 |
| 5,599,801 A | 2/1997 | Branellec et al. ............ | 514/56 |
| 5,618,917 A | 4/1997 | Toback et al. ............... | 530/350 |
| 5,619,421 A | 4/1997 | Venkataraman et al. .... | 364/496 |
| 5,681,733 A | 10/1997 | Su et al. ...................... | 435/232 |
| 5,687,090 A | 11/1997 | Chen et al. | |
| 5,714,376 A | 2/1998 | Sasisekharan et al. ... | 435/252.3 |
| 5,744,515 A | 4/1998 | Clapper ...................... | 523/113 |
| 5,752,019 A | 5/1998 | Rigoutsos et al. | |
| 5,753,445 A | 5/1998 | Fillit et al. ................... | 435/7.1 |
| 5,763,427 A | 6/1998 | Weitz et al. .................. | 514/56 |
| 5,795,875 A | 8/1998 | Holme et al. ................ | 514/56 |
| 5,808,021 A | 9/1998 | Holme et al. ................ | 536/21 |
| 5,824,299 A | 10/1998 | Luster et al. ............. | 424/85.1 |
| 5,830,726 A | 11/1998 | Sasisekharan et al. ... | 435/172.3 |
| 5,856,928 A | 1/1999 | Yan | |
| 5,919,693 A | 7/1999 | Su et al. .................. | 435/252.3 |
| 5,922,358 A | 7/1999 | Doutremepuich et al. .. | 424/553 |
| 5,952,653 A * | 9/1999 | Covey et al. ............... | 250/288 |
| 5,997,863 A | 12/1999 | Zimmermann et al. .... | 424/94.5 |
| 6,013,628 A | 1/2000 | Skubitz et al. ................ | 514/12 |
| 6,217,863 B1 | 4/2001 | Godavarti et al. | |
| 6,268,146 B1 * | 7/2001 | Shultz et al. .................. | 435/6 |
| 6,309,853 B1 * | 10/2001 | Friedman et al. .......... | 435/69.1 |
| 6,333,051 B1 * | 12/2001 | Kabanov et al. ............ | 424/484 |

OTHER PUBLICATIONS

Alderman, C. et al., "Continuous Subcutaneous Heparin Infusion for Treatment of Trousseau's Syndrome", *Ann Pharmacother,* Jul.–Aug. 1995, 29:(7–8):710–713.

Baumann, U. et al., "Three–dimensional structure of the alkaline protease of Pseudomonas aeruginosa:a two–domain protein with a calcium binding parallel beta roll motif", *The EMBO Journal,* vol. 12, No. 9, pp. 3357–3364, 1993.

Bernstein, H. et al., "Immobilized Heparin Lyase System for Blood Deheparinization", *Methods in Enzymology,* vol. 137, pp. 515–529, 1988.

Cardin, A.D. et al., "Molecular Modeling of Protein–Glycosaminoglycan Interactions", *Arteriosclerosis,* vol. 9, No. 1, Jan./Feb. 1989, pp. 21–32.

Cohen, F. E., "The Parallel β Helix of Pectate Lyase C: Something to Sneeze At", *Science,* vol. 260, Jun. 4, 1993, pp. 1444–1445.

Comfort, A.R. et al., "Immobilized Enzyme Cellulose Hollow Fibers: III. Physical Properties and In Vitro Biocompatibility", *Biotechnology and Bioengineering,* vol. 34, pp. 1383–1390, 1989.

Feingold, D.S. et al., Conformational aspects of the reaction mechanisms of polysaccharide lyases and epimerases, *FEBS Letters,* vol. 223, No. 2, Nov., 1987, pp. 207–211.

Franklin, M.J. et al., "Pseudomonas Aeruginosa AlgG is a Polymer Level Alginate C5–Mannuronan Epimerase", *Journal of Bacteriology,* vol. 176, No. 7, Apr. 1994, pp. 1821–1830.

Gacesa, P., "Alginate–modifying enzymes—A proposed unified mechanism of action for the lyases and epimerases", *FEBS Letters,* vol. 212, No. 2, feb. 1987, pp. 199–202.

Godavarti R. et al., "Heparinase I from Flavobacterium heparinum. Identification of a Critical Histidine Residue Essential for Catalysis as Probed by Chemical Modification and Site–Directed Mutagensis", *Biochemistry,* vol. 35, No. 21, 1996, pp. 6846–6852.

Enriquez–Harris, P. et al., "Growth Factors and the Extracellular Matrix", *Meeting Report,* Trends in Cell Biology, 1994.

Hart, G. W., "Glycosylation", *Current Opinion in Cell Biology,* 1992, 4:1017–1023.

Higuchi, R.., "Recombinant PCT", *PCR Protocols: A Guide to Methods and Applications, Academic Press, Inc.,* 1990, pp. 177–183.

Huang, J.N. et al., "Low–Molecular–Weight Heparins", *Coagulation Disorders,* vol. 12, No. 6, Dec. 1998, pp. 1251–1277.

Jackson, R.L., et al., "Glycosaminoglycans: Molecular Properties, Protein Interactions, and Role in Physiological Processes", *Reviews,* vol. 71, No. 2, Apr. 1991, pp. 481–539.

Kakkar, A. et al., "Venous Thromboembolism and Cancer", *Baillieres Clin Haematol,* Sep. 1998, 11(3):675–687.

Kretsinger, R.H. et al., "Structure and Evolution of Calcium–Modulated Proteins", *CRC Critical Reviews in Biochemistry,* vol. 8, Issue 2, Jul. 1980, pp. 119–174.

Leckband, D. et al., "An Approach for the Stable Immobilization of Proteins", *Biotechnology and Bioengeering,* (1991), vol. 37, pp. 227–237.

Leckband, D. et al., "Characterization of the Active Site of Heparinase", Abstracts for Papers from the Fourth Chemical Congress of North America, vol. 202, No. 1, Aug. 1991, New York, p. a56.

Lewin, B., "Cells Obey the Laws of Physics and Chemistry", *GENES V,* 1994, p. 13.

Linhardt, R.J. et al., "Review Polysaccharide Lyases", *Applied Biochemistry and Biotechnology,* vol. 12, 1986, pp. 135–176.

Linhardt, R.J. et al., "Examination of the Substrate Specificity of Heparin and Heparan Sulfate Lyases", *Biochemistry,* vol. 29, No. 10, 1990, pp. 2611–2617.

Linhardt, R.J. et al., "Production and Chemical Processing of Low Molecular Weight Heparins", *Seminars in Thrombosis and Hemostasis,* vol. 25, Suppl. 3, 1999, pp. 5–16.

Lohse, D.L. et al., "Purification and Characterization of Heparin Lyases from *Flavobacterium heparinum*", *The Journal of Biological Chemistry,* vol. 267, No. 34, Issue of Dec. 5, 1992, pp. 24347–24355.

Lustig, F. et al., "Alternative Splicing Determines the Binding of Platelet–Derived Growth Factor (PDGF–AA) to Glycosaminoglycans", *Biochemistry,* vol. 35, No. 37, 1996, pp. 12077–12085.

Sasisekharan, R. et al., "Cloning and expression of heparinase I gene from *Flavobacterium heparinum*", *Proc Natl Acad Sci USA,* vol. 90, pp. 3660–3664, Apr. 1993.

Sasisekharan, R. et al., "Heparinase inhibits neovascularization", Proc Natl Acad Sci USA, vol. 91, pp. 1524–1528, Feb. 1994.

Sasisekharan, R. et al., "Heparinase I from *Flavobacterium heparinum:* The Role of the Cysteine Residue in Catalysis as Probed by Chemical Modification and Site–Directed Mutagenesis", *Biochemistry,* vol. 34, No. 44, pp. 14441–14448, 1995.

Sasisekharan, R. et al., "Heparinase I from Flavobacterium heparinum", *The Journal of Biological Chemistry,* vol. 271, No. 6, Issue Feb. 9, 1996, pp. 3124–3131.

Shriver, Z. et al., "Heparinase II from Flavobacterium heparinum: Role of Histidine Residues in Enzymatic Activity as Probed by Chemical Modification and Site–Directed Mutagenesis", *The Journal of Biological Chemistry,* vol. 273, No. 17, Apr. 1998, pp. 10160–10167.

Shriver , Z. et al., "Heparinase II from Flavorbacterium heparinum: Role of Cysteine in Enzymatic Activity as Probed by Chemical Modification and Site–Directed Mutagenesis," *The Journal of Biological Chemistry,* vol. 273, No. 36, Sep. 1998, pp. 22904–22912.

Valentine, K.A. et al., "Low–Molecular–Weight Heparin Therapy and Mortality", *Seminars in Thrombosis and Hemostasis,* vol. 23, No. 2, 1997, pp. 173–178.

Yang, V.C. et al., "Purification and Characterization of Heparinase from *Flavobacterium heparinum"*, *The Journal of Biological Chemistry,* vol. 260, No. 3, Feb. 1985, pp. 1849–1857.

Yoder, M.D. et al., "Unusual structural features in the parallel β–helix in pectate lyases", *Structure,* Dec. 1993, vol. 1, No. 4, pp. 241–251.

Yoder, M.D. et al., "New Domain Motif: The Structure of Pectate Lyase C., a Secreted Plant Virulence Factor", *Science,* vol. 260, pp. 1503–1506, Jun. 4, 1993.

Zucharski, L. et al., "Blood Coagulation Activation in Cancer: Challenges for Cancer Treatment", *Hamostaseologie,* 1995, 15:14–20.

Yan et al, Prime Numbers and the Amino Acid Code: Analogy in Coding Properties, J. Theor. Biol. (1991) 151, 333–341.

Rudd et al., "Oligosaccharide Sequencing Technology" Nature, vol. 388, No. 6638, Jul. 10, 1997, pp. 205–207.

Zhao et al, "Rapid, sensitive structure analysis of oligosaccharides", Proc. Natl. Acad. Sci, vol. 94, pp. 1629–1633, Mar. 1997.

Brian Hayes, "Prototeins", American Scientist, vol. 86, May–Jun. 1998, pp. 216–221.

Ernst et al, "Direct evidence for a predominantly exolytic processive mechanism for depolymerization of heparin–like glycosamineoglycans by heparinase" Proc. Natl. Acad. Sci., vol. 95. pp. 4182–4197, Apr. 1998.

* cited by examiner

METHOD FOR INDENTIFYING OR CHARACTERIZING PROPERTIES OF POLYMERIC UNITS

RELATED APPLICATION

This application claims priority under 35 U.S.C. §119 to U.S. Provisional Patent Application No. 60/130,747, filed Apr. 23, 1999, No. 60/130,792, filed Apr. 23, 1999, No. 60/159,939, filed Oct. 14, 1999, and No. 60/159,940, filed Oct. 14, 1999, each of which are incorporated herein by reference in their entirety.

BACKGROUND

Various notational systems have been used to encode classes of chemical units by assigning a unique code to each chemical unit in the class. For example, a conventional notational system for encoding amino acids assigns a single letter of the alphabet to each known amino acid. A polymer of chemical units may be represented using such a notational system using a set of codes corresponding to the chemical units. Such notational systems have been used to encode polymers, such as proteins, in a computer-readable format. A polymer that has been represented in such a computer-readable format according to a notational system may be stored and processed by a computer.

Conventional notational schemes for representing chemical units have represented the chemical units as characters (e.g., A, T, G, and C for nucleic acids), and have represented polymers of chemical units as sequences or sets of characters. Various operations may be performed on such a notational representation of a chemical unit or a polymer comprised of chemical units. For example, a user may search a database of chemical units for a query sequence of chemical units. In such a case, the user typically provides a character-based notational representation of the sequence in the form of a sequence of characters, which is compared against the character-based notational representations of sequences of chemical units stored in the database. Character-based searching algorithms, however, are typically slow because such algorithms search by comparing individual characters in the query sequence against individual characters in the sequences of chemical units stored in the database. The spread of such algorithms is therefore related to the length of the query sequence, resulting in particularly poor performance for long query sequences.

The study of molecular and cellular biology is focused on the macroscopic structure of cells. We now know that cells have a complex microstructure that determine the functionality of the cell. Much of the diversity associated with cellular structure and function is due to the ability of a cell to assemble various building blocks into diverse chemical compounds. The cell accomplishes this task by assembling polymers from a limited set of building blocks referred to as monomers. The key to the diverse functionality of polymers is based in the primary sequence of the monomers within the polymer and is integral to understanding the basis for cellular function, such as why a cell differentiates in a particular manner or how a cell will respond to treatment with a particular drug.

The ability to identify the structure of polymers by identifying their sequence of monomers is integral to the understanding of each active component and the role that component plays within a cell. By determining the sequences of polymers it is possible to generate expression maps, to determine what proteins are expressed, to understand where mutations occur in a disease state, and to determine whether a polysaccharide has better function or loses function when a particular monomer is absent or mutated.

SUMMARY

Polymers may be characterized by identifying properties of the polymers and comparing those properties to reference polymers, a process referred to herein as property encoded nomenclature (PEN). In one embodiment, the properties are encoded using a binary notation system, and the comparison is accomplished by comparing the binary representations of polymers. For instance, in one aspect a sample polymer is subjected to an experimental constraint to modify the polymer, the modified polymer is compared to a reference database of polymers to identify a population of polymers having a property that is the same as or similar to a property of the sample polymer. The method may be repeated until the population of polymers in the reference database is reduced to one and the identity of the sample polymer is known.

In a system including a database of properties of polymers of chemical units a method for determining the composition of a sample polymer of chemical units having a known molecular weight and length is provided according to one aspect of the invention. The method includes the steps of (A) selecting, from the database, candidate polymers of chemical units having the same length as the sample polymer of chemical units and having molecular weights similar to the molecular weight of the sample polymer of chemical units;

(B) performing an experiment on the sample polymer of chemical units;

(C) measuring properties of the sample polymer of chemical units resulting from the experiment; and (D) eliminating, from the candidate polymers of chemical units, polymers of chemical units having properties that do not correspond to the experimental results.

In some embodiments the method also includes the step of:

(E) repeatedly performing the step (D) until the number of candidate polymers of chemical units falls below a predetermined threshold.

In other aspects the invention is a method for identifying a population of polymers of chemical units having the same property as a sample polymer of chemical units. The method includes the steps of determining a property of a sample polymer of chemical units, and comparing the property of the sample polymer to a reference database of polymers of known sequence and known properties to identify a population of polymers of chemical units having the same property as a sample polymer of chemical units, wherein the reference database of polymers includes identifiers corresponding to the chemical units of the polymers, each of the identifiers including a field storing a value corresponding to the property.

In one embodiment the step of determining a property of the sample polymer involves the use of mass spectrometry, such as for example, matrix assisted laser desorption ionization mass spectrometry (MALDI-MS), electron spray-MS, fast atom bombardment mass spectrometry (FAB-MS) and collision-activated dissociation mass spectrometry (CAD) to determine the molecular weight of the polymer. MALDI-MS, for instance, may be used to determine the molecular weight of the polymer with an accuracy of approximately one Dalton.

The step of identifying a property of the polymer in other embodiments may involve the reduction in size of the polymer into pieces of several units in length that may be detected by strong ion exchange chromatography. The fragments of the polymer may be compared to the reference database polymers.

According to other aspects, the invention is a method for identifying a subpopulation of polymers having a property in common with a sample polymer of chemical units. The method involves the steps of applying an experimental constraint to the polymer to modify the polymer, detecting a property of the modified polymer, identifying a population of polymers of chemical units having the same molecular length as the sample polymer, and identifying a subpopulation of the identified population of polymers having the same property as the modified polymer by eliminating, from the identified population of polymers, polymers having properties that do not correspond to the modified polymer. The steps may be repeated on the modified polymer to identify a second subpopulation within the subpopulation of polymers having a second property in common with the twice modified polymer. Each of the steps may then be repeated until the number of polymers within the subpopulation falls below a predetermined threshold. The method may be performed to identify the sequence of the polymer. In this case the predetermined threshold of polymers within the subpopulation is two polymers.

In yet another aspect, the invention is a method for identifying a subpopulation of polymers having a property in common with a sample polymer of chemical units. The method involves the steps of applying an experimental constraint to the polymer to modify the polymer, detecting a first property of the modified polymer, identifying a population of polymers of chemical units having a second property in common with the sample polymer, and identifying a subpopulation of the identified population of polymers having the same first property as the modified polymer by eliminating, from the identified population of polymers, polymers having properties that do not correspond to the modified polymer.

In one embodiment the experimental constraints applied to the polymer are different for each repetition. The experimental constrain may be any manipulation which alters the polymer in such a manner that it will be possible to derive structural information about the polymer or a unit of the polymer. In some embodiments the experimental constraint applied to the polymer may be any one or more of the following constraints: enzymatic digestion, e.g., with an exoenzyme, an endoenzyme, a restriction endonuclease; chemical digestion; chemical modification; interaction with a binding compound; chemical peeling (i.e., removal of a monosaccharide unit); and enzymatic modification, for instance sulfation at a particular position with a heparin sulfate sulfotransferases.

The property of the polymer that is detected by the method of the invention may be any structural property of a polymer or unit. For instance the property of the polymer may be the molecular weight or length of the polymer. In other embodiments the property may be the compositional ratios of substituents or units, type of basic building block of a polysaccharide, hydrophobicity, enzymatic sensitivity, hydrophilicity, secondary structure and conformation (i.e., position of helices), spatial distribution of substituents, ratio of one set of modifications to another set of modifications (i.e., relative amounts of 2-O sulfation to N-sulfation or ratio of iduronic acid to glucuronic acid, and binding sites for proteins.

The properties of the modified polymer may be detected in any manner possible which depends on the property and polymer being analyzed. In one embodiment the step of detection involves mass spectrometry such as matrix assisted laser desorption ionization mass spectrometry (MALDI-MS), electron spray MS, fast atom bombardment mass spectrometry (FAB-MS) and collision-activated dissociation mass spectrometry (CAD). Alternatively, the step of detection involves strong ion exchange chromatography, for example, if the polymer has been digested into several smaller fragments composed of several units each.

The method is based on a comparison of the sample polymer with a population of polymers of the same length or having at least one property in common. In some embodiments the population of polymers of chemical units includes every polymer sequence having the molecular weight of the sample polymer. In other embodiments the population of polymers of chemical units includes less than every polymer sequence having the molecular weight of the sample polymer. According to some embodiments the step of identifying includes selecting the population of polymers of chemical units from a database including molecular weights of polymers of chemical units. Preferably the database includes identifiers corresponding to chemical units of a plurality of polymers, each of the identifiers including a field storing a value corresponding to a property of the corresponding chemical unit.

According to another aspect of the invention a method for compositional analysis of a sample polymer is provided. The method includes the steps of applying an experimental constraint to the sample polymer to modify the sample polymer, detecting a property of the modified sample polymer, and comparing the modified sample polymer to a reference database of polymers of identical size as the polymer, wherein the polymers of the reference database have also been subjected to the same experimental constraint as the sample polymer, wherein the comparison provides a compositional analysis of the sample polymer.

In some embodiments the compositional analysis reveals the number and type of units within the polymer. In other embodiments the compositional analysis reveals the identity of a sequence of chemical units of the polymer.

Similarly to the aspects of the invention described above the properties of the polymer may be detected in any manner possible and will depend on the particular property and polymer being analyzed. In one embodiment the step of detection involves mass spectrometry such as matrix assisted laser desorption ionization mass spectrometry (MALDI-MS), electron spray MS, fast atom bombardment mass spectrometry (FAB-MS) and collision-activated dissociation mass spectrometry (CAD). Preferably the experimental constraint applied to the polymer is an enzymatic or chemical reaction which involves incomplete enzymatic digestion of the polymer and wherein the steps of the method are repeated until the number of polymers within the reference database falls below a predetermined threshold. Alternatively, the step of detection involves capillary electrophoresis, particularly when the experimental constraint applied to the polymer involves complete degradation of the polymer into individual chemical units.

In one embodiment the reference database includes identifiers corresponding to chemical units of a plurality of polymers, each of the identifiers including a field storing a value corresponding to a property of the corresponding chemical unit.

According to yet another aspect of the invention a method for sequencing a polymer is provided. The method includes the steps of applying an experimental constraint to the polymer to modify the polymer, detecting a property of the modified polymer, identifying a population of polymers having the same molecular length as the sample polymer and having molecular weights similar to the molecular weight of the sample polymer, identifying a subpopulation of the identified population of polymers having the same property as the modified polymer by eliminating, from the identified population of polymers, polymers having properties that do not correspond to the modified polymer, and repeating the steps applying an experimental constraint, detecting a property and identifying a subpopulation by applying additional experimental constraints to the polymer and identifying additional subpopulations of polymers until the number of polymers within the subpopulation is one and the sequence of the polymer may be identified.

In another aspect the invention relates to a method for identifying a polysaccharide-protein interaction, by contacting a protein-coated MALDI surface with a polysaccharide containing sample to produce a polysaccharide-protein-coated MALDI surface, removing unbound polysaccharide from the polysaccharide-protein-coated MALDI surface, and performing MALDI mass spectrometry to identify the polysaccharide that specifically interacts with the protein coated on the MALDI surface.

In one embodiment a MALDI matrix is added to the polysaccharide-protein-coated MALDI surface. In other embodiments an experimental constraint may be applied to the polysaccharide bound on the polysaccharide-protein-coated MALDI surface before performing the MALDI mass spectrometry analysis. The experimental constraint applied to the polymer in some embodiments is digestion with an exoenzyme or digestion with an endoenzyme. In other embodiments the experimental constraint applied to the polymer is selected from the group consisting of restriction endonuclease digestion; chemical digestion; chemical modification; and enzymatic modification.

Each of the limitations of the invention can encompass various embodiments of the invention. It is, therefore, anticipated that each of the limitations of the invention involving any one element or combinations of elements may be included in each aspect of the invention.

DETAILED DESCRIPTION

Figure 1:
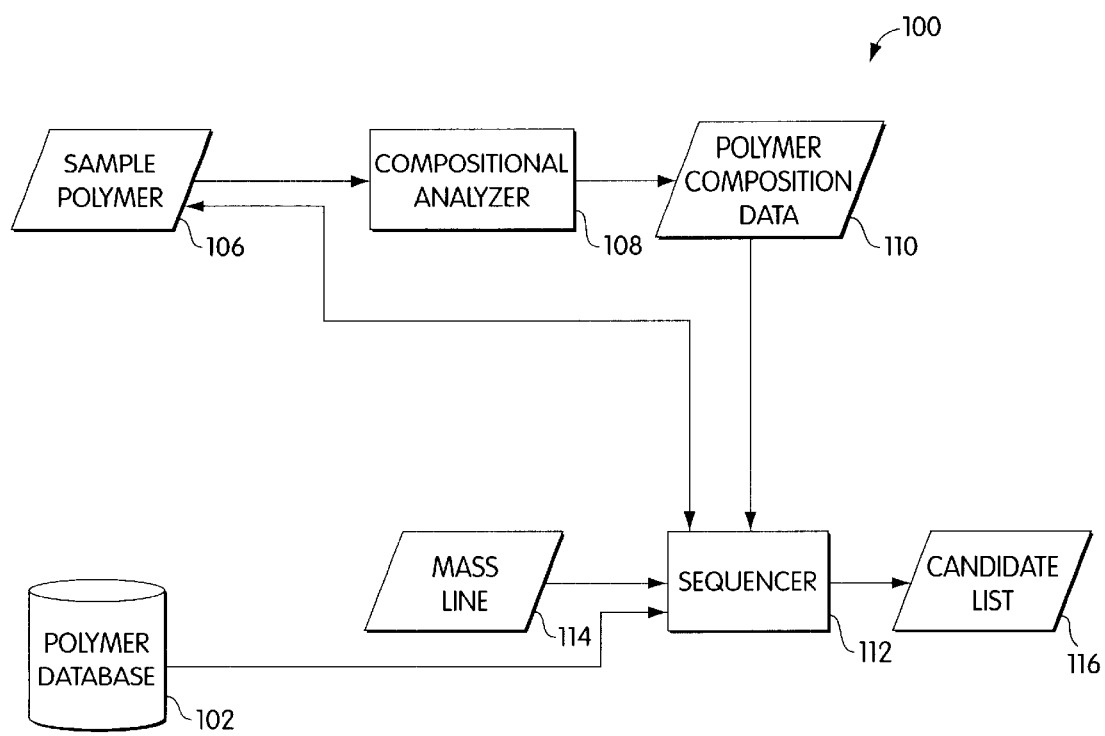
FIG. 1 is a dataflow diagram of a system for sequencing a polymer.

The invention relates in some aspects to methods for characterizing polymers to identify structural properties of the polymers, such as the charge, the nature and number of units of the polymer, the nature and number of chemical substituents on the units, and the stereospecificity of the polymer. The structural properties of polymers may provide useful information about the function of the polymer. For instance, the properties of the polymer may reveal the entire sequence of units of the polymer, which is useful for identifying the polymer. Similarly, if the sequence of the polymer was previously unknown, the structural properties of the polymer are useful for comparing the polymer to known polymers having known functions. The properties of the polymer may also reveal that a polymer has a net charge or has regions which are charged. This information is useful for identifying compounds that the polymer may interact with or predicting which regions of a polymer may be involved in a binding interaction or have a specific function.

Many methods have been described in the prior art for identifying polymers and in particular for identifying the sequence of units of polymers. Once the sequence of a polymer is identified the sequence information is stored in a database and may be used to compare the polymer with other sequenced polymers. Databases such as GENBANK enable the storage and retrieval of information relating to the sequences of nucleic acids which have been identified by researchers all over the world. These databases typically store information using notational systems that encode classes of chemical units by assigning a unique code to each chemical unit in the class. For example, a conventional notational system for encoding amino acids assigns a single letter of the alphabet to each known amino acid. Such databases represent a polymer of chemical units using a set of codes corresponding to the chemical units. Searches of such databases have typically been performed using character-based comparison algorithms.

New methods for identifying structural properties of polymers which can utilize Bioinformatics and which differ from the prior art methods of assigning a character to each unit of a polymer have been discovered. These methods are referred to as PEN (property encoded nomenclature). In one aspect, the invention is based on the identification and characterization of properties of a polymer, rather than units of the polymer, and the use of numeric identifiers to classify those properties and to facilitate information processing relating to the polymer.

The ability to identify properties of polymers and to manipulate the information concerning the properties of the polymer provide many advantages over prior art methods of characterizing polymers and Bioinformatics. For instance, the methods of the invention may be used to identify structural information and analyze complex polymers such as polysaccharides which were previously very difficult to analyze using prior art methods.

The heterogeneity and the high degree of variability of the polysaccharide building blocks have hindered prior art attempts to sequence these complex molecules. With the advent of extremely sensitive techniques like High Pressure Liquid Chromatography (HPLC), Capillary Electrophoresis (CE) and Mass Spectrometry (MS) to isolate and characterize large biomolecules, significant advances have been made in isolating and purifying polysaccharide fragments containing specific sequences but extensive experimental manipulation is still required to identify and sequence information. Additionally, in most of these approaches, plenty of information about the sequence is required in order to design the experimental manipulations that will enable the sequencing of the polysaccharide. The methods of the prior art provide simple and rapid methods for identifying sequence information. Many other advantages will be clear from the description of the preferred embodiments set forth below.

A "polymer" as used herein is a compound having a linear and/or branched backbone of chemical units which are secured together by linkages. In some but not all cases the backbone of the polymer may be branched. The term "backbone" is given its usual meaning in the field of polymer chemistry. The polymers may be heterogeneous in backbone composition thereby containing any possible combination of polymer units linked together such as peptide- nucleic acids. In some embodiments the polymers are homogeneous in backbone composition and are, for example, a nucleic acid, a polypeptide, a polysaccharide, a carbohydrate, a polyurethane, a polycarbonate, a polyurea, a polyethyleneimine, a polyarylene sulfide, a polysiloxane, a polyimide, a polyacetate, a polyamide, a polyester, or a polythioester. A "polysaccharide" is a biopolymer comprised of linked saccharide or sugar units. A "nucleic acid" as used herein is a biopolymer comprised of nucleotides, such as deoxyribose nucleic acid (DNA) or ribose nucleic acid (RNA). A polypeptide as used herein is a biopolymer comprised of linked amino acids.

As used herein with respect to linked units of a polymer, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the chemical units of a particular polymer, are most common. Natural linkages include, for instance, amide, ester and thioester linkages. The chemical units of a polymer analyzed by the methods of the invention may be linked, however, by synthetic or modified linkages. Polymers where the units are linked by covalent bonds will be most common but also include hydrogen bonded, etc.

The polymer is made up of a plurality of chemical units. A "chemical unit" as used herein is a building block or monomer which may be linked directly or indirectly to other building blocks or monomers to form a polymer. The polymer preferably is a polymer of at least two different linked units. The particular type of unit will depend on the type of polymer. For instance DNA is a biopolymer comprised of a deoxyribose phosphate backbone composed of units of purines and pyrimidines such as adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. RNA is a biopolymer comprised of a ribose phosphate backbone composed of units of purines and pyrimidines such as those described for DNA but wherein uracil is substituted for thymidine. DNA units may be linked to the other units of the polymer by their 5' or 3' hydroxyl group thereby forming an ester linkage. RNA units may be linked to the other units of the polymer by their 5', 3' or 2' hydroxyl group thereby forming an ester linkage. Alternatively, DNA or RNA units having a terminal 5', 3' or 2' amino group may be linked to the other units of the polymer by the amino group thereby forming an amide linkage.

Whenever a nucleic acid is represented by a sequence of letters it will be understood that the nucleotides are in 5'→3' order from left to right and that "A" denotes adenosine, "C" denotes cytidine, "G" denotes guanosine, "T" denotes thymidine, and "U" denotes uracil unless otherwise noted.

The chemical units of a polypeptide are amino acids, including the 20 naturally occurring amino acids as well as modified amino acids. Amino acids may exist as amides or free acids and are linked to the other units in the backbone of the polymers through their a-amino group thereby forming an amide linkage to the polymer.

A polysaccharide is a polymer composed of monosaccharides linked to one another. In many polysaccharides the basic building block of the polysaccharide is actually a disaccharide unit which may be repeating or non-repeating. Thus, a unit when used with respect to a polysaccharide refers to a basic building block of a polysaccharide and may include a monomeric building block (monosaccharide) or a dimeric building block (disaccharide).

A "plurality of chemical units" is at least two units linked to one another.

The polymers may be native or naturally-occurring polymers which occur in nature or non-naturally occurring polymers which do not exist in nature. The polymers typically include at least a portion of a naturally occurring polymer. The polymers may be isolated or synthesized de novo. For example, the polymers may be isolated from natural sources e.g. purified, as by cleavage and gel separation or may be synthesized e.g.,(i) amplified in vitro by, for example, polymerase chain reaction (PCR); (ii) synthesized by, for example, chemical synthesis; (iii) recombinantly produced by cloning, etc.

The invention is useful for identifying properties of polymers. A "property" as used herein is a characteristic (e.g., structural characteristic) of the polymer that provides information (e.g., structural information) about the polymer. When the term property is used with respect to any polymer except a polysaccharide the property provides information other than the identity of a unit of the polymer or the polymer itself. A compilation of several properties of a polymer may provide sufficient information to identify a chemical unit or even the entire polymer but the property of the polymer itself does not encompass the chemical basis of the chemical unit or polymer.

When the term property is used with respect to polysaccharides, to define a polysaccharide property, it has the same meaning as described above except that due to the complexity of the polysaccharide, a property may identify a type of monomeric building block of the polysaccharide. Chemical units of polysaccharides are much more complex than chemical units of other polymers, such as nucleic acids and polypeptides. The polysaccharide unit has more variables in addition to its basic chemical structure than other chemical units. For example, the polysaccharide may be acetylated or sulfated at several sites on the chemical unit, or it may be charged or uncharged. Thus, one property of a polysaccharide may be the identity of one or more basic building blocks of the polysaccharides.

A basic building block alone, however, may not provide information about the charge and the nature of substituents of the saccharide or disaccharide. For example, a building block of uronic acid may be iduronic or glucuronic acid. Each of these building blocks may have additional substituents that add complexity to the structure of the chemical unit. A single property, however, may not identify such additional substitutes charges, etc., in addition to identifying a complete building block of a polysaccharide. This information, however, may be assembled from several properties. Thus, a property of a polymer as used herein does not encompass an amino acid or nucleotide but does encompass a saccharide or disaccharide building block of a polysaccharide.

The type of property that will provide structural information about a polymer will depend on the type of polymer being analyzed. For instance, if the polymer is a polysaccharide a property such as charge, molecular weight, nature and degree of sulfation or acetylation, or type of saccharide will provide structural information about the polymer. If the polymer is a polypeptide then a property will provide information about charge, acidity, etc. Properties include but are not limited to charge, chirality, nature of substituents, quantity of substituents, molecular weight, molecular length, compositional ratios of substituents or units, type of basic building block of a polysaccharide, hydrophobicity, enzymatic sensitivity, hydrophilicity, secondary structure and conformation (i.e., position of helices), spatial distribution of substituents, ratio of one set of modifications to another set of modifications (i.e., relative amounts of 2-O sulfation to N-sulfation or ratio of iduronic acid to glucuronic acid, and binding sites for proteins. Other properties will easily be identified by those of ordinary skill in the art. A substituent, as used herein is an atom or group of atoms that substitute a unit, but are not themselves the units.

The property of the polymer may be identified by any means known in the art. The procedure used to identify the property will depend on the type of property. Molecular weight, for instance, may be determined by several methods including mass spectrometry. The use of mass spectrometry for determining the molecular weight of polymers is well known in the art. Mass Spectrometry has been used as a powerful tool to characterize polymers because of its accuracy (±1 Dalton) in reporting the masses of fragments generated e.g. by enzymatic cleavage and also because only pM sample concentrations are required. For instance matrix-assisted laser desorption ionization mass spectrometry (MALDI-MS) has been described for identifying the molecular weight of polysaccharide fragments in publications such as Rhomberg, A. J. et al, *PNAS, USA*, v. 95, p. 4176–4181 (1998); Rhomberg, A. J. et al, *PNAS, USA*, v. 95, p. 12232–12237 (1998); and Ernst, S. et. al., *PNAS, USA*, v. 95, p. 4182–4187 (1998), each of which is hereby incorporated by reference. Other types of mass spectrometry known in the art, such as, electron spray-MS, fast atom bombardment mass spectrometry (FAB-MS) and collision-activated dissociation mass spectrometry (CAD) may also be used to identify the molecular weight of the polymer or polymer fragments.

Figure 5:
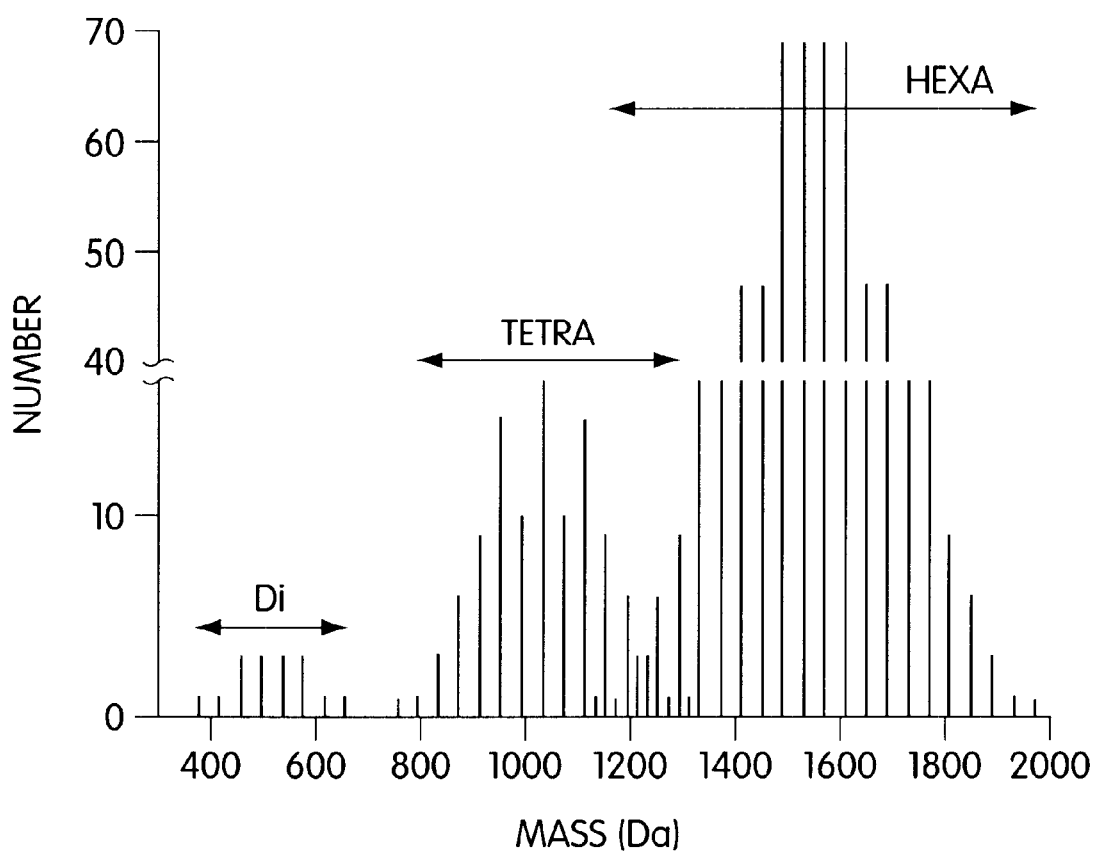
FIG. 5 is a mass line diagram.

The mass spectrometry data may be a valuable tool to ascertain information about the polymer fragment sizes after the polymer has undergone degradation with enzymes or chemicals. After a molecular weight of a polymer is identified, it may be compared to molecular weights of other known polymers. Because masses obtained from the mass spectrometry data are accurate to one Dalton (1 D), a size of one or more polymer fragments obtained by enzymatic digestion may be precisely determined, and a number of substituents (i.e., sulfates and acetate groups present) may be determined. One technique for comparing molecular weights is to generate a mass line and compare the molecular weight of the unknown polymer to the mass line to determine a subpopulation of polymers which have the same molecular weight. A "mass line" as used herein is an information database, preferably in the form of a graph or chart which stores information for each possible type of polymer having a unique sequence based on the molecular weight of the polymer. Thus, a mass line may describe a number of polymers having a particular molecular weight. A two-unit nucleic acid molecule (i.e., a nucleic acid having two chemical units) has 16 (4 units$^2$) possible polymers at a molecular weight corresponding to two nucleotides. A two-unit polysaccharide (i.e., disaccharide) has 32 possible polymers at a molecular weight corresponding to two saccharides. Thus, a mass line may be generated by uniquely assigning a particular mass to a particular length of a given fragment (all possible di, tetra, hexa, octa, up to a hexadecasaccharide), and tabulating the results (An Example is shown in FIG. 5).

Table 1 below shows an example of a computed set of values for a polysaccharide. From Table 1, a number of chemical units of a polymer may be determined from the minimum difference in mass between a fragment of length n+1 and a fragment of length n. For example, if the repeat is a disaccharide unit, a fragment of length n has 2n monosaccharide units. For example, n=1 may correspond to a length of a disaccharide and n=2 may correspond to a length of a tetrasaccharide, etc.

TABLE 1

| Fragment Length n | Minimum difference in mass between n + 1 and n (D (Dalton)) |
|---|---|
| 1 | 101.13 |
| 2 | 13.03 |
| 3 | 13.03 |
| 4 | 9.01 |
| 5 | 9.01 |
| 6 | 4.99 |
| 7 | 4.99 |
| 8 | 0.97 |
| 9 | 0.97 |

Because mass spectrometry data indicates the mass of a fragment to 1 D accuracy, a length may be assigned uniquely to fragment by looking up a mass on the mass line. Further, it may be determined from the mass line that, within a fragment of particular length higher than a disaccharide, there is a minimum of 4.02 D different in masses indicating that two acetate groups (84.08 D) replaced a sulfate group (80.06 D). Therefore, a number of sulfates and acetates of a polymer fragment may be determined from the mass from the mass spectrometry data and, such number may be assigned to the polymer fragment.

In addition to molecular weight, other properties may be determined using methods known in the art. The compositional ratios of substituents or chemical units (quantity and type of total substituents or chemical units) may be determined using methodology known in the art, such as capillary electrophoresis. A polymer may be subjected to an experimental constraint such as enzymatic or chemical degradation to separate each of the chemical units of the polymers. These units then may be separated using capillary electrophoresis to determine the quantity and type of substituents or chemical units present in the polymer. Additionally, a number of substituents or chemical units can be determined using calculations based on the molecular weight of the polymer.

In the method of capillary gel-electrophoresis, reaction samples may be analyzed by small-diameter, gel-filled capillaries. The small diameter of the capillaries (50 $\mu$m) allows for efficient dissipation of heat generated during electrophoresis. Thus, high field strengths can be used without excessive Joule heating (400 V/m), lowering the separation time to about 20 minutes per reaction run, therefor increasing resolution over conventional gel electrophoresis. Additionally, many capillaries may be analyzed in parallel, allowing amplification of generated polymer information.

In addition to being useful for identifying a property, compositional analysis also may be used to determine a presence and composition of an impurity as well as a main property of the polymer. Such determinations may be accomplished if the impurity does not contain an identical composition as the polymer. To determine whether an impurity is present may involve accurately integrating an area under each peak that appears in the electrophoretogram and normalizing the peaks to the smallest of the major peaks. The sum of the normalized peaks should be equal to one or close to being equal to one. If it is not, then one or more impurities are present. Impurities even may be detected in unknown samples if at least one of the disaccharide units of the impurity differs from any disaccharide unit of the unknown.

If an impurity is present, one or more aspects of a composition of the components may be determined using capillary electrophoresis. Because all known disaccharide units may be baseline-separated by the capillary electrophoresis method described above and because migration times typically are determined using electrophoresis (i.e., as opposed to electroosmotic flow) and are reproducible, reliable assignment to a polymer fragment of the various saccharide units may be achieved. Consequently, both a composition of the major peak and a composition of a minor contaminant may be assigned to a polymer fragment. The composition for both the major and minor components of a solution may be assigned as described below.

One example of such assignment of compositions involves determining the composition of the major AT-III binding HLGAG decasaccharide (+DDD4−7) and its minor contaminant (+D5D4−7) present in solution in a 9:1 ratio. Complete digestion of this 9:1 mixture with a heparinases yields 4 peaks: three representative of the major decasaccharide (viz., D, 4, and −7) which are also present in the contaminant and one peak, 5, that is present only in the contaminant. In other words, the area of each peak for D, 4, and −7 represents an additive combination of a contribution from the major decasaccharide and the contribution from the contaminant, whereas the peak for 5 represents only the contaminant.

To assign the composition of the contaminant and the major component, the area under the 5 peak may be used as a starting point. This area represents an area under the peak for one disaccharide unit of the contaminant. Subtracting this area from the total area of 4 and −7 and subtracted twice this area from an area under D yields a 1:1:3 ratio of 4:−7:D. Such a ratio confirms the composition of the major component and indicates that the composition of the impurity is two Ds, one 4, one −7 and one 5.

Methods of identifying other types of properties may be easily identifiable to those of skill in the art and may depend on the type of property and the type of polymer. For example, hydrophobicity may be determined using reverse-phase high-pressure liquid chromatography (RP-HPLC). Enzymatic sensitivity may be identified by exposing the polymer to an enzyme and determining a number of fragments present after such exposure. The chirality may be determined using circular dichroism. Protein binding sites may be determined by mass spectrometry, isothermal calorimetry and NMR. Enzymatic modification (not degradation) may be determined in a similar manner as enzymatic degradation, i.e., by exposing a substrate to the enzyme and using MALDI-MS to determine if the substrate is modified. For example, a sulfotransferase may transfer a sulfate group to an HS chain having a concomitant increase in 80 Da. Conformation may be determined by modeling and nuclear magnetic resonance (NMR). The relative amounts of sulfation may be determined by compositional analysis or approximately determined by Raman spectroscopy.

In some aspects the invention is useful for generating, searching and manipulating information about polymers. In this aspect the complete building block of a polymer is assigned a unique numeric identifier, which may be used to classify the complete building block. For instance if a polysaccharide is being analyzed, each numeric identifier would represent a complete building block of a polysaccharide, including the exact chemical structure as defined by the basic building block of a polysaccharide and all of its substituents, charges etc. A basic building block refers to a basic structure of the polymer unit e.g., a basic ring structure of a polysaccharide, such as iduronic acid or glucuronic acid but does not include substituents, charges etc. The information is generated and processed in the same manner as described above with respect to "properties" of polymers.

Currently, saccharide fragments are detected in capillary electrophoresis by monitoring at 232 nm, the wavelength at which the $\Delta^{4,5}$ double bond, generated upon heparinase cleavage, absorbs. However, other detection methods are possible. First, nitrous acid cleavage of heparin fragments, followed by reduction with $^3$H-sodium borohydride yields degraded fragments having a $^3$H radioactive tag. This represents both a tag which may be followed by capillary electrophoresis (counting radioactivity) or mass spectrometry (by the increase in mass). Another method of using radioactivity would be to label the heparin fragment with $S^{35}$. Similar to the types of detection possible for $^3$H-labeled fragments, $S^{35}$ labeled fragments may be useful for radioactive detection (CE) or measurement of mass differences (MS).

Especially in the case of $S^{35}$, this detection will be powerful. In this case, the human sulfotransferases may be used to label specifically a certain residue. This will give additional structural information.

Nitrous acid degraded fragments, unlike heparinase-derived fragments, do not have a UV-absorbing chromophore. As we have shown, MALDI-MS will record the mass of heparin fragments regardless of how they are derived. For CE, two methods may be used to monitor fragments that lack a suitable chromophore. First is indirect detection of fragments. We may detect heparin fragments with our CE methodology using a suitable background absorber, e.g., 1,5-napthalenedisulfonic acid. The second method for detection involves chelation of metal ions by saccharides. The saccharide-metal complexes may be detected using UV-Vis just like monitoring the unsaturated double bond.

Other groups have begun the process of raising antibodies to specific HLGAG sequences. We have previously shown that proteins, e.g., angiogenin, FGF, may be used as the complexing agent instead of a synthetic, basic peptide. By extension, antibodies could be used as a complexing agent for MALDI-MS analysis. This enables us to determine whether specific sequences are present in an unknown sample simply by observing whether a given antibody with a given sequence specificity complexes with the unknown using MALDI-MS.

The final point is that using mass tags, we may distinguish the reducing end of a glycosaminoglycan from the non-reducing end. All of these tags involve selective chemistry with the anomeric OH (present at the reducing end of the polymer), thus labeling occurs at the reducing end of the chain. One common tag is 2-aminobenzoic acid which is fluorescent. In general tags involve chemistry of the following types: (1) reaction of amines with the anomeric position to form imines (i.e., 2-aminobenzoic acid), hydrazine reaction to form hydrazones, and reaction of semicarbazones with the anomeric OH to form semicarbazides. Commonly used tags (other than 2-aminobenzoic acid) include the following compounds:
1. semicarbazide
2. Girard's P reagent
3. Girard's T reagent
4. p-aminobenzoic ethyl ester
5. biotin-x-hydrazide
6. 2-aminobenzamide
7. 2-aminopyridine
8. anthranilic acid
9. 5-[(4,6-dichlorotriazine-2-yl)amino]-fluorescein
10. 8-aminonaphthalene-1,3,6-trisulfonic acid
11. 2-aminoacridone Referring to FIG. 1, a system 100 for sequencing polymers is shown. The system 100 includes a polymer database 102 which includes a plurality of records storing information corresponding to a plurality of polymers. Each of the records may store information about properties of the corresponding polymer, properties of the corresponding polymer's constituent chemical units, or both. The polymers for which information is stored in the polymer database 102 may be any kind of polymers. For example, the polymers may include polysaccharides, nucleic acids, or polypeptides. In one embodiment, each of the records in the polymer database 102 includes a polymer identifier (ID) that identifies the polymer corresponding to the record. The record also includes chemical unit identifiers (IDs) corresponding to chemical units that are constituents of the polymer corresponding to the record. Polymers may be represented in the polymer database in other ways. For example, records in the polymer database 102 may include only a polymer ID or may only include chemical unit IDs.

The polymer database 102 may be any kind of storage medium capable of storing information about polymers as described herein. For example, the polymer database 102 may be a flat file, a relational database, a table in a database, an object or structure in a computer-readable volatile or non-volatile memory, or any data accessible to a computer program, such as data stored in a resource fork of an application program file on a computer-readable storage medium.

In one embodiment, a polymer ID includes a plurality of fields for storing information about properties of the polymer corresponding to the record containing the polymer ID. Similarly, in one embodiment, chemical unit IDs include a plurality of fields for storing information about properties of the chemical unit corresponding to the chemical unit ID. Although the following description refers to the fields of chemical unit Ids, such description is equally applicable to the fields of polymer IDs.

The fields of chemical unit IDs may store any kind of value that is capable of being stored in a computer readable medium, such as a binary value, a hexadecimal value, an integral decimal value, or a floating point value. The fields may store information about any properties of the corresponding chemical unit.

A compositional analyzer 108 receives as input a sample polymer 106 and generates as output polymer composition data 110 that is descriptive of the composition of the sample polymer. A compositional analyzer as used herein is any type of equipment or experimental procedure that may be used to identify a property of a polymer modified by an experiment constraint, such as those described above. These include, for instance, but are not limited to capillary electrophoresis, mass spectrometry, and chromatography. The polymer composition data 110 includes information about the sample polymer 106, such as the properties of the chemical units in the sample polymer 106 and the number of chemical units in the sample polymer 106. A sequencer 112 generates a candidate list 116 of a subpopulation of polymers that might match the sample polymer 106 in the process of sequencing the sample polymer 106 using information contained in a mass line 114 and the polymer database 102. A candidate list is also referred to herein as a "population" of polymers. At the end of the sequencing process, the candidate list 116 contains zero or more polymers that correspond to the sample polymer 106. A subpopulation of polymers is defined as a set of polymers having at least two properties in common with a sample polymer. It is useful to identify subpopulations of polymers in order to have an information set with which to compare the sample polymer 106.

Consider, for example, the sequence DD7DAD-7, which is a tetradecasaccharide (14 mer) of HLGAG containing 20 sulfate groups. The compositional analyzer 108 may, for example, perform compositional analysis of DD7DAD-7 by degrading the sequence to its disaccharide building blocks and analyzing the relative abundance of each unit using capillary electrophoresis to generate the polymer composition data 110. The polymer composition data 110 in this case would show a major peak corresponding to ±D, a peak about ½ the size of the major peak corresponding to ±7 and another peak about ¼ the size of the major peak corresponding to ±A. Note that the ± sign is used because degradation by heparinase would create a double bond between the C4 and C5 atoms in the uronic acid ring thereby leading to the loss of the iduronic vs. glucuronic acid information. From the polymer composition data 110, it may be inferred that there are 4±Ds, 2±7s and a ±A in the sequence.

Figure 2:
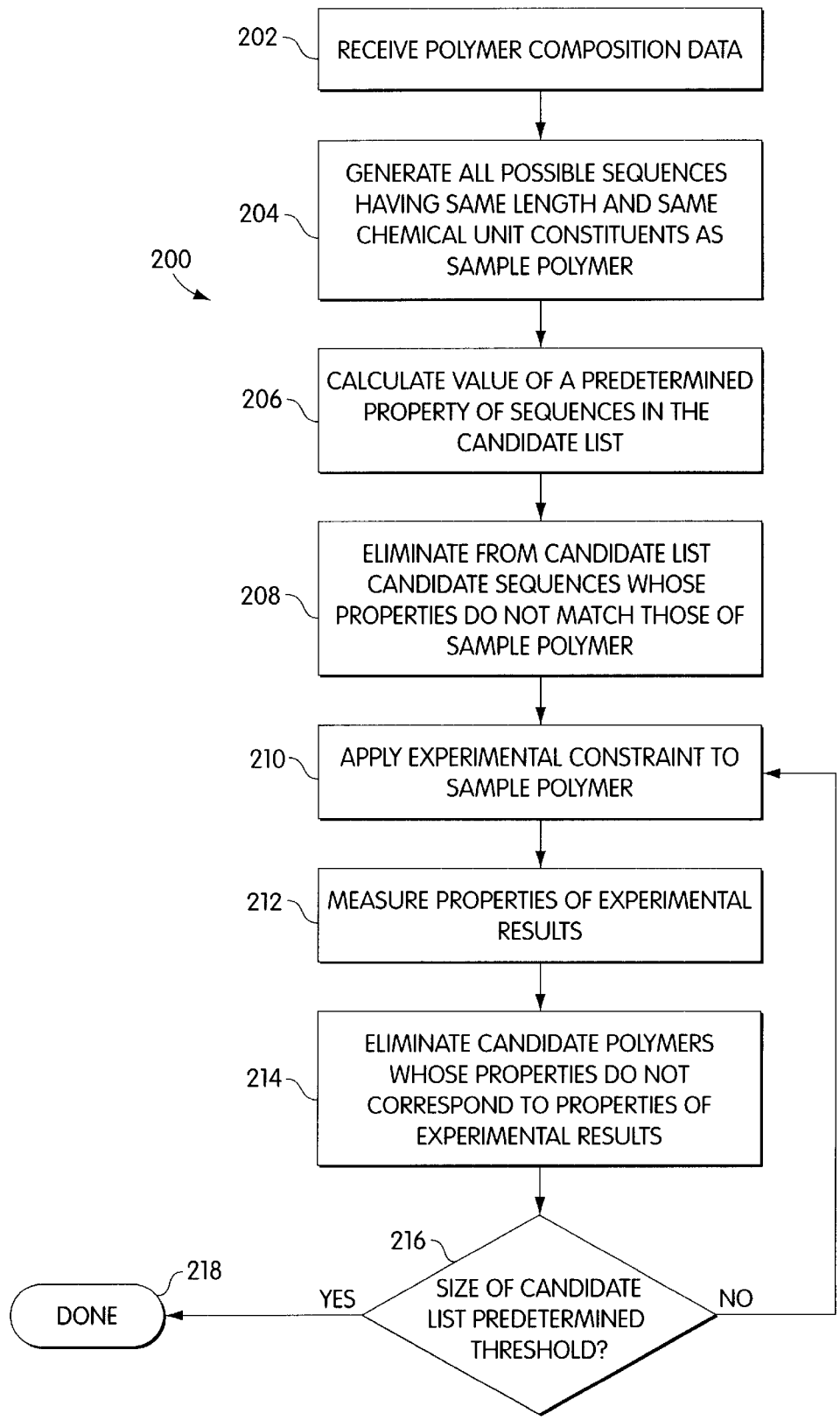
FIG. 2 is a flow chart of a process for sequencing a polymer.

Referring to FIG. 2, a process 200 that may be performed by the sequencer 112 to sequence the sample polymer 106 is shown. The sequencer 112 receives the polymer composition data 110 from the compositional analyzer 108. The sequencer 112 uses the polymer composition data 110 and the information contained in the polymer database 102 to generate an initial candidate list 116 of all possible polymers: (1) having the same length as the sample polymer 106 and (2) having the same constituent chemical units as the sample polymer 106 (step 204).

For example, consider the sequence DD7DAD-7 mentioned above. The polymer composition data 110 indicates that the sequence includes 4±Ds, 2±7s and one ±A, and indicates that the length of the sample polymer 106 is seven. In this case, step 204 (generation of the candidate list 116) involves generating all possible sequences having the same length as the sample polymer 106 and having 4±Ds, 2±7s and a ±A. In one embodiment, the sequencer 112 uses a brute force method to generate all sequences having these characteristics by generating all sequences of length seven having 4±Ds, 2±7s and a ±A using standard combinatoric methods.

The sequencer 112 then uses the data from the mass line 114 to progressively eliminate sequences from the list generated in step 204 until the number of sequences in the list reaches a predetermined threshold (e.g., one). To perform such elimination, in one embodiment, the sequencer 112 calculates the value of a predetermined property of each of the polymers in the candidate list 116 (step 206). The predetermined property may, for example, be the mass of the polymer. An example method for calculating the mass of a polymer will be described in more detail below. The sequencer 112 compares the calculated values of the predetermined property of the polymers in the candidate list 116 to the value of the predetermined property of the sample polymer 106 (step 208). The sequencer 112 eliminates candidate polymers from the candidate list 116 whose predetermined property values do not match the value of the predetermined property of the sample polymer 106 within a predetermined range (step 208). For example, if the predetermined property is molecular weight, the predetermined range may be ±1.5 D.

The sequencer 112 applies an experimental constraint to the sample polymer 106 to modify the sample polymer 106 (step 210). An "experimental constraint" as used herein is a biochemical process performed on a polymer which results in modification to the polymer which may be detected. Experimental constraints include but are not limited to enzymatic digestion, e.g., with an exoenzyme, an endoenzyme, a restriction endonuclease; chemical digestion; chemical modification; interaction with a binding compound; chemical peeling (i.e., removal of a monosaccharide unit); and enzymatic modification, for instance sulfation at a particular position with a heparan sulfate sulfotransferases.

The sequencer 112 measures properties of the modified sample polymer 106 (step 212). The sequencer 112 eliminates from the candidate list 116 those candidate polymers having property values that do not match the property values of the experimental results 122 (step 214).

If the size of the candidate list 116 is less than a predetermined threshold (e.g., 1) (step 216), then the sequencer 112 is done (step 218). The contents of the candidate list 116 at this time represent the results of the sequencing process. The candidate list 116 may contain zero or more polymers, depending upon the contents of the polymer database 102 and the value of the predetermined threshold. If the size of the candidate list 116 is not less than the predetermined threshold (step 216), steps 210-216 are repeated until the size of the candidate list 116 falls below the predetermined threshold. When the sequencer 112 is done (step 218), the sequencer 112 may, for example, display the candidate list 116 to the user on an output device such as a computer monitor.

Figure 3:
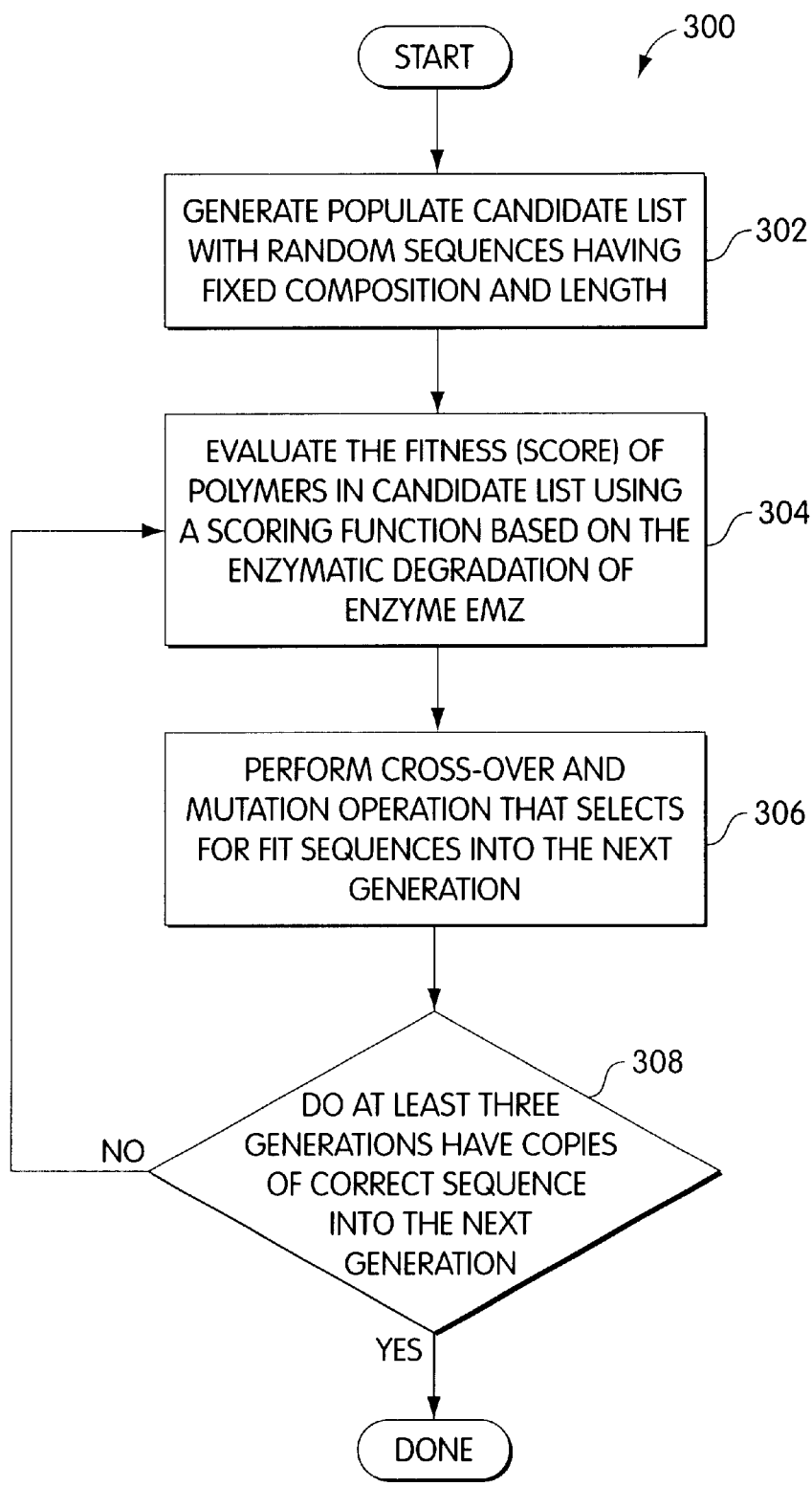
FIG. 3 is a flow chart of a process for sequencing a polymer using a genetic algorithm.

Referring to FIG. 3, in another embodiment, the sequencer 112 uses a genetic algorithm process 300 to generate the initial candidate list 116 and to modify the candidate list 116 in order to arrive at a final candidate polymer that identifies the sequence of the sample polymer 106. The sequencer 112 generates a population of random sequences with the composition indicated by the polymer composition data 110 and having the same length as the sample polymer 106 (step 302). The sequencer 112 evaluates the fitness (score) of the polymers in the candidate list 116 using a scoring function based on the enzymatic degradation of enzyme ENZ (step 304). The genetic algorithm process 300 uses the fitness values to decide which of the sequences in the candidate list 116 can survive into the next generation and which of the sequences in the candidate list 116 has the highest chance of producing other sequences of equal or higher fitness by cross-over and mutation. The sequencer 112 then performs cross-over and mutation operations that select for fit sequences in the candidate list 116 into the next generation (step 306). If at least a predetermined number (e.g., three) of generations of the candidate list 116 include copies of the correct sequence with the maximum fitness (step 308), then the sequencer 112 is done sequencing. Otherwise, the sequencer 112 repeats steps 304-306 until the condition of step 308 is satisfied. Cross-over and mutation operations are used by genetic algorithms to randomly sample the different regions of a search space.

In one embodiment, steps 210 and 212 are automated (e.g., carried out by a computer). For example, after the initial candidate list 116 has been generated (step 208), the sequencer 112 may divide the candidate list 116 into categories (the categories are preferably based on properties), such as hepI cleavable, hepIII cleavable, and nitrous acid cleavable (the property is enzymatic sensitivity). The sequencer 112 may then simulate the corresponding degradation or modification of the sequences present in each of the categories and search for those sequences that give fragments of unique masses. Based on the population of sequences that can give fragments of unique masses upon degradation or modification, the sequencer 112 chooses the particular enzyme or chemical as the experimental constraint to eliminate candidate polymers from the candidate list 116 (step x). Although in this example only hepI, hepIII, and nitrous acid are used, other experimental constraints such as enzymes may be used including the exoenzymes and other HLGAG degrading chemicals.

In another embodiment, the sequencer 112 uses a chemical characteristic to guide the choice of experimental constraint. For example, normalized frequencies of chemical units of known polymers containing $I_{2S}$, G, $H_{NS}$, and $H_{Nac}$ may be calculated. For example, the normalized frequency $f(I_{2S})$ of chemical units containing $I_{2S}$ may be calculated as $f(I_{2S})$=(number of disaccharide units containing $I_{2S}$)/ (number of disaccharide units). An example set of normalized frequencies calculated for known sequences in this way is shown in table 2 below.

TABLE 2

| Sequence | $f(I_{2S})$ | $f(G)$ | $f(H_NS)$ | $f(H_{NAc})$ | Constraints used for convergence |
|---|---|---|---|---|---|
| Octa2 DDD-5 | 0.75 | 0.25 | 1 | 0 | Hep I and Hep III degradation |

TABLE 2-continued

| Sequence | f(I₂S) | f(G) | f(HNS) | f(HNAc) | Constraints used for convergence |
|---|---|---|---|---|---|
| FGF binding DDDDD | 1 | 0 | 1 | 0 | Hep I normal and exhaustive degradation |
| ATIII binding DDD4-7 | 0.6 | 0.2 | 0.8 | 0.2 | Hep I, Hep II and nitrous acid degradation |

The "constraints used for convergence" column indicates constraints that have been shown empirically to achieve convergence for the corresponding known sequence. Once compositional analysis has been performed on a sample (unknown) polymer, the relative frequencies of $I_{2S}$, G, $H_{NS}$, and $H_{NAc}$ in the sample sequence may be compared to the relative frequencies of the known sequences using the table above. To select a set of experimental constraints to apply to the sample polymer, the relative frequencies of the sample polymer may be compared to the relative frequencies of the known sequences in the. table above. A known sequence with relative frequencies that are similar to the relative frequencies of the sample polymer may then be selected, and the experimental constraints identified with the selected sequence (as shown in the table) may then be applied to the sample polymer.

For example, Table 2 demonstrates that the presence of f(G) and f($H_{NAc}$) are important factors in the decision to use hepIII and nitrous acid, because nitrous acid clips after a $H_{NS}$, and hepIII clips after a disaccharide unit containing G. The disaccharide unit $I_{2S}$-$H_{NS,6}$S is the dominant unit in heparin-like regions (i.e., highly-sulfated regions) of the HLGAG chains. Therefore, if a sequence is more heparin-like, then hepI may be chosen as the default enzyme and the information content present in chemical units containing G and $H_{NAc}$ become important for choosing enzymes and chemicals other than hepI. Similarly, for low-sulfated regions on HLGAG chains, hepIII may be a default enzyme and f($I_{2S}$) and f($H_{NS}$) become important for choosing hepI and nitrous acid. Similarly, one may also calculate the positional sulfate or acetate distribution along the chain and generate the criterion for using the sulfotransferases or sulfateases for convergence.

In one embodiment, the polymer database 102 stores the mass of each polymer in the polymer database 102. In this embodiment, step 206 (described above) may be performed merely by retrieving the mass of the corresponding polymer from the polymer database 102. In another embodiment, the polymer database 102 includes information indicating a mass of a baseline polymer. For example, in one embodiment the polymer database 102 stores information about disaccharides. Referring to Table 3, which illustrates one use of a binary notational representation system to notate disaccharides, it may be seen that the mass of the I-$H_{NAc}$ disaccharide unit is 379.33 D.

TABLE 3

| I/G | 2X | 6X | 3X | NX | ALPH CODE | DISACC | MASS (ΔU) |
|---|---|---|---|---|---|---|---|
| 0 | 0 | 0 | 0 | 0 | 0 | I-H_NAc | 379.33 |
| 0 | 0 | 0 | 0 | 1 | 1 | I-H_NS | 417.35 |
| 0 | 0 | 0 | 1 | 0 | 2 | I-H_NAc,3S | 459.39 |
| 0 | 0 | 0 | 1 | 1 | 3 | I-H_NS,3S | 497.41 |
| 0 | 0 | 1 | 0 | 0 | 4 | I-H_NAc,6S | 459.39 |
| 0 | 0 | 1 | 0 | 1 | 5 | I-H_NS,6S | 497.41 |

TABLE 3-continued

| I/G | 2X | 6X | 3X | NX | ALPH CODE | DISACC | MASS (ΔU) |
|---|---|---|---|---|---|---|---|
| 0 | 0 | 1 | 1 | 0 | 6 | I-H_NAc,3S,6S | 539.45 |
| 0 | 0 | 1 | 1 | 1 | 7 | I-H_NS,3S,6S | 577.47 |
| 0 | 1 | 0 | 0 | 0 | 8 | I₂S-H_NAc | 459.39 |
| 0 | 1 | 0 | 0 | 1 | 9 | I₂S-H_NS | 497.41 |
| 0 | 1 | 0 | 1 | 0 | A | I₂S-H_NAc,3S | 539.45 |
| 0 | 1 | 0 | 1 | 1 | B | I₂S-H_NS,3S | 577.47 |
| 0 | 1 | 1 | 0 | 0 | C | I₂S-H_NAc,6S | 539.45 |
| 0 | 1 | 1 | 0 | 1 | D | I₂S-H_NS,6S | 577.47 |
| 0 | 1 | 1 | 1 | 0 | E | I₂S-H_NAc,3S,6S | 619.51 |
| 0 | 1 | 1 | 1 | 1 | F | I₂S-H_NS,3S,6S | 657.53 |
| 1 | 0 | 0 | 0 | 0 | -0 | G-H_NAc | 379.33 |
| 1 | 0 | 0 | 0 | 1 | -1 | G-H_NS | 417.35 |
| 1 | 0 | 0 | 1 | 0 | -2 | G-H_NAc,3S | 459.39 |
| 1 | 0 | 0 | 1 | 1 | -3 | G-H_NS,3S | 497.41 |
| 1 | 0 | 1 | 0 | 0 | -4 | G-H_NAc,6S | 459.39 |
| 1 | 0 | 1 | 0 | 1 | -5 | G-H_NS,6S | 497.41 |
| 1 | 0 | 1 | 1 | 0 | -6 | G-H_NAc,3S,6S | 539.45 |
| 1 | 0 | 1 | 1 | 1 | -7 | G-H_NS,3S,6S | 577.47 |
| 1 | 1 | 0 | 0 | 0 | -8 | G₂S-H_NAc | 459.39 |
| 1 | 1 | 0 | 0 | 1 | -9 | G₂S-H_NS | 497.41 |
| 1 | 1 | 0 | 1 | 0 | -A | G₂S-H_NAc,3S | 539.45 |
| 1 | 1 | 0 | 1 | 1 | -B | G₂S-H_NS,3S | 577.47 |
| 1 | 1 | 1 | 0 | 0 | -C | G₂S-H_NAc,6S | 539.45 |
| 1 | 1 | 1 | 0 | 1 | -D | G₂S-H_NS,6S | 577.47 |
| 1 | 1 | 1 | 1 | 0 | -E | G₂S-H_NAc,3S,6S | 619.51 |
| 1 | 1 | 1 | 1 | 1 | -F | G₂S-H_NS,3S,6S | 657.53 |

In addition to the hexadecimal codes used in table 1 the following extra symbols were used to represent modifications in the disaccharide building block: 5-membered anhydromannitol ring–'; uronic acid with a C4–C5 unsaturated linkage–±; reducing end disaccharide unit with a mass tag–(superscript) t; disaccharide unit without the uronic acid–*.

The polymer database 102 may include information indicating that sulfation at a position of a polymer contributes 80.06 D to the mass of the polymer and that substitution of a sulfate for an acetate contributes an additional 38.02 D to the mass of the polymer. Therefore, the mass M of any polymer in the polymer database 102 may be calculated using the following formula:

$$M=379.33+[0\ 80.06\ 80.06\ 80.06\ 38.02]*C,$$

where C is the vector containing the binary representation of the polymer and * is a vector multiplication operator. For example, the mass of the disaccharide unit $I_{2S}$-$H_{NS,6S}$, having a binary representation of 01101, would be equal to 379.33+[0 80.06 80.06 80.06 38.02 ]*[01101]=379.33+0+ 80.06*1+80.06*1+80.06*0+38.02*1=577.47 D.

Although the invention encompasses all polymers, the use of the invention is described in more detail with respect to polysaccharides because of the complex nature of polysaccharides. The invention, however, is not limited to polysaccharides. The heterogeneity of the heparin-like-glycosaminoglycan (HLGAG) fragments and the high degree of variability in their saccharide building blocks have hindered the attempts to sequence these complex molecules.

Heparin-like-glycosaminoglycans (HLGAGs) which include heparin and heparan sulfate are complex polysaccharide molecules made up of disaccharide repeat units of hexoseamine and glucuronic/iduronic acid that are linked by α/β 1–4 glycosidic linkages. These defining units may be modified by sulfation at the N, 3-O and 6-O position of the hexoseamine, 2-O sulfation of the uronic acid and C5 epimerization that converts the glucuronic acid to iduronic acid. Schematically the disaccharide unit of HLGAG may be represented as

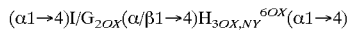

where

X may be sulfated (—SO3H) or unsulfated (—H)

Y may be sulfated (—SO3H) or acetylated (—COCH3)

HLGAGs may be represented using a notational system in which an HLGAG is represented by a polymer ID (described above). The fields of the polymer ID may store any kinds of values, such as single-bit values, single-digit hexadecimal values, or decimal values. In one embodiment, the polymer ID representing an HLGAG includes each of the following fields: (1) a field for storing a value indicating whether the polymer contains an iduronic or a glucuronic acid (I/G); (2) a field for storing a value indicating whether the 2X position of the iduronic or glucuronic acid is sulfated or unsulfated; (3) a field for storing a value indicating whether the hexoseamine is sulfated or unsulfated; (4) a field indicating whether the 3X position of the hexoseamine is sulfated or unsulfated; and (5) a field indicating whether the NX position of the hexoseamine is sulfated or acetylated.

In one embodiment, each of the fields is represented as a single bit. An example of the use of this scheme to encode HLGAGs is shown in Table 1. Bit values for each of the fields may be assigned in any manner. For example, with respect to the I/G field, in one embodiment a value of one indicates Iduronic and a value of zero indicates Glucuronic, while in another embodiment a value of one indicates Glucuronic and a value of zero indicates Iduronic.

In one embodiment, the four fields (2X, 6X, 3X, and NX) is represented as a single hexadecimal (base 16) number where each of the four fields represents one of the bits of the hexadecimal number. Using hexadecimal numbers to represent disaccharide units is convenient both for representation and processing because hexadecimal digits are a common form of representation used by conventional computers. In a further embodiment, the five fields (I/G, 2X, 6X, 3X, NX) are represented as a signed hexadecimal digit, in which the four fields (2X, 6X, 3X, NX) are used to code a single-digit hexadecimal number as described above and the I/G field is used as a sign bit. In this embodiment, the hexadecimal numbers 0–F may be used to code units containing iduronic acid and the hexadecimal numbers –0 to –F may be used to code units containing glucuronic acid. The polymer unit ID may, however, be encoded in other ways, such as by using a twos-complement representation.

HLGAG fragments may be degraded using enzymes such as heparin lyase enzymes or nitrous acid and they may also be modified using different enzymes that transfer sulfate groups to the positions mentioned earlier or remove the sulfate groups from those positions. The modifying enzymes are exolytic and non-processive which means that they just act once on the non reducing end and will let go of the heparin chain without sequentially modifying the rest of the chain. For each of the modifiable positions in the disaccharide unit there exits a modifying enzyme. An enzyme that adds a sulfate group is called a sulfotransferase and an enzyme that removes a sulfate group is called a sulfatase. The modifying enzymes include 2-O sulfatase/sulfotransferase, 3-O sulfatase/sulfotransferase, 6-O sulfatase/sulfotransferase and N-deacetylase-N-sulfotransferase. The function of these enzymes is evident from their names, for example a 2-O sulfotransferase transfers a sulfate group to the 2-O position of an iduronic acid (2-O sulfated glucuronic acid is a rare occurrence in the HLGAG chains) and a 2-O sulfatase removes the sulfate group from the 2-O position of an iduronic acid.

HLGAG degrading enzymes include heparinase-I, heparinase-II, heparinase-III, D-glucuronidase and L-iduronidase. The heparinases cleave at the glycosidic linkage before a uronic acid. Heparinase I clips at a glycosidic linkage before a 2-O sulfated iduronic acid. Heparinase-III cleaves at a glycosidic linkage before an unsulfated glucuronic acid. Heparinase-II cleaves at both Hep-I and Hep-III cleavable sites. After cleavage by the heparinases the uronic acid before which the cleavage occurs loses the information of iduronic vs. glucuronic acid because a double bond is created between the C4 and C5 atoms of the uronic acid.

Glucuronidase and iduronidase, as their name suggests cleave at the glycosidic linkage after a glucuronic acid and iduronic acid respectively. Nitrous acid clips randomly at glycosidic linkages after a N-sulfated hexosamine and converts the six membered hexosamine ring to a 5 membered anhydromannitol ring.

The above rules for the enzymes may easily be encoded into a computer as described above using binary arithmetic so that the activity of an enzyme on a sequence may be carried out using simple binary operators to give the fragments that would be formed from the enzymatic activity.

These techniques may be used to construct a database of polysaccharide sequences. In some aspects the invention is a database of polysaccharide sequences, as well as, motif search and sequence alignment algorithms for obtaining valuable information about the nature of polysaccharide-protein interactions that are vital for the biological functioning of these molecules. The sequence information in the database of polysaccharide sequences may also be used to provide valuable insight into sequence-structure relationships of these molecules.

In addition to the use of the methods of the invention for sequencing polymers, the methods may be used for any purpose in which it is desirable to identify structural properties related to a polymer. For instance the methods of the invention may be used for analysis of low molecular weight heparin. By limited digestion of LMWH and analysis by CE and MALDI-MS, we may obtain an "digest spectrum" of various preparations of LMWH, thus deriving information about the composition and variations thereof. Such information is of value in terms of quality control for LMWH preparations.

The methods are also useful for understanding the role of HLGAGs in fundamental biological processes. Already MS has been used to look at the presence of various proteins as a function of time in Drosophila development. In a similar fashion HLGAG expression can be as a function both of position and of time in Drosophila development. Similarly the methods may be used as a diagnostic tool for human diseases. There is a group of human diseases called mucopolysaccharidosis (MPS). The molecular basis for these diseases is mostly in the degradation pathway for HLGAGs. For instance, mucopolysaccharidosis type I involves a defect in iduronidase, which clips unsulfated iduronate residues from HLGAG chains. Similarly, persons suffering from mucopolysaccharidosis type II (MPS II) lack iduronate-2-sulfatase. In each of these disorders, marked changes in the composition and sequence of cell surface HLGAGs occurs. Our methodology could be used as a diagnostic for these disorders to identify which MPS syndrome a patient is suffering from.

Additionally the methods of the invention are useful for mapping protein binding HLGAG sequences. Analogous to fingerprinting DNA, the MALDI-MS sequencing approach may be used to specifically map HLGAG sequences that bind to selected proteins. This is achieved by sequencing the HLGAG chain in the presence of a target protein as well as in the absence of the particular protein. In this manner, sequences protected from digestion are indicative of sequences that bind with high affinity to the target protein.

Figure 4A:
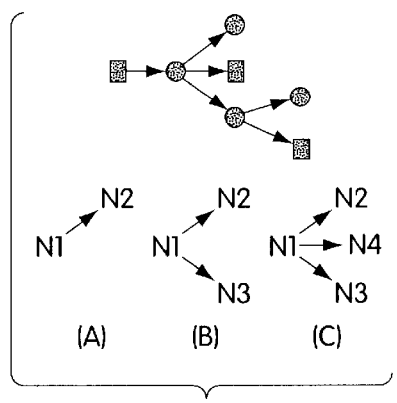
FIGS. 4A–D is a set of diagrams depicting notation schemes for branched chain analysis.

The methods of the invention may be used to analyze branched or unbranched polymers. Analysis of branched polymers is more difficult than analysis of unbranched polymers because branched carbohydrates, are "information dense" molecules. Branched polysaccharides include a few building blocks that can be combined in several different ways, thereby, coding for many sequences. For instance, a trisaccharide, in theory, can give rise to over 6 million different sequences. The methods for analyzing branched polysaccharides, in particular, are advanced by the creation of an efficient nomenclature that is amenable to computational manipulation. Thus, an efficient nomenclature for branched sugars that is amenable to computational manipulation has been developed according to the invention. Two types of numerical schemes that may encode the sequence information of these polysaccharides has been developed in order to bridge the widely used graphic (pictorial) representation and the proposed numerical scheme discussed below.

a. Byte-based (Binary-scheme) notation scheme: The first notation scheme is based on a binary numerical system. The binary representation in conjunction with a tree-traversing algorithm is used to represent all the possible combinations of the branched polysaccharides. The nodes (branch points) are easily amenable to computational searching through tree-traversing algorithms (FIG. 4A). FIG. 4A shows a notation scheme for branched sugars. Each monosaccharide unit can be represented as a node (N) in a tree. The building blocks can be defined as either (A), (B), or (C) where N1, N2, N3, and N4 are individual monosaccharides. Each of these combinations can be coded numerically to represent building blocks of information. By defining glycosylation patterns in this way, there are several tree traversal and searching algorithms in computer science that may be applied to solve this problem.

Figure 4B:
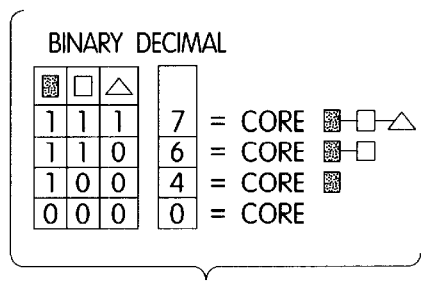
Figure 4C:
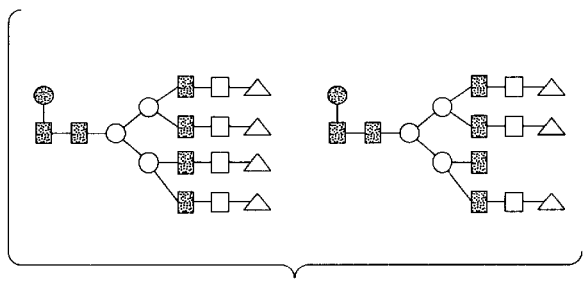

A simpler version of this notational scheme is shown in FIG. 4B. This simplified version may be extended to include all other possible modifications including unusual structures. For examples, an N-linked glycosylation in vertebrates contains a core region (the tri-mannosyl chitobiose moiety), and up to four branched chains from the core. In addition to the branched chains the notation scheme also includes other modification (such as addition of fucose to the core, or fucosylation of the GlcNac in the branches or sialic acid on the branches). Thus, the superfamily of N-linked polysaccharides can be broadly represented by three modular units: a) core region: regular, fucosylated and/or bisected with a GlcNac., b) number of branches: up to four branched chains, each with GlcNac, Gal and Neu., and c) modifications of the branch sugars. These modular units may be systematically combined to generate all possible combinations of the polysaccharide. Representation of the branches and the sequences within the branches can be performed as a n-bit binary code (0 and 1) where n is the number of monosaccharides in the branch. FIG. 4C depicts a binary code containing the entire information regarding the branch. Since there are up to four branches possible, each branch can be represented by a 3-bit binary code, giving a total of 12 binary bits. The first bit represents the presence (binary 1) or absence (binary 0) of the GlcNac residue adjoining the mannose. The second and the third bit similarly represent the presence or absence of the Gal and the Neu residues in the branch. Hence a complete chain containing GlcNac-Gal-Neu is represented as binary (111) which is equivalent to decimal 7. Four of the branches can then be represented by a 4 bit decimal code, the $1^{st}$ bit of the decimal code for the first branch and the $2^{nd}$, the second branch etc (right).

This simple binary code does not contain the information regarding the linkage (α vs. β and the 1-6 or 1-3 etc.) to the core. This type of notation scheme, however, may be easily expanded to include additional bits for branch modification. For instance, the presence of a 2-6 branched neuraminic acid to the GlcNac in the branch can be encoded by a binary bit.

b. Prime Decimal Notation Scheme: Similar to the binary notation described above, a second computationally friendly numerical system, which involves the use of a prime number scheme, has been developed. The algebra of prime numbers is extensively used in areas of encoding, cryptography and computational data manipulations. The scheme is based on the theorem that for small numbers, there exists a uniquely-definable set of prime divisors. In this way, composition information may be rapidly and accurately analyzed.

This scheme is illustrated by the following example. The prime numbers 2, 3, 5, 7, 11, 13, 17, 19, and 23 are assigned to nine common building blocks of polysaccharides. The composition of a polysaccharide chain may then be represented as the product of the prime decimals that represent each of the building blocks. For illustration, GlcNac is assigned the number 3 and mannose the number 2. The core is represented in this scheme as 2×2×2×3×3=72 (3 mannose and 2 GlcNacs). This notation, therefore, relies on the mathematical principle that 72 can be ONLY expressed as the combination of three 2s and two 3s. The prime divisors are therefore unique and can encode the composition information. This becomes a problem when one gets to very large numbers but not an issue for the size of numbers we encounter in this analysis. From this number the mass of the polysaccharide chain can be determined.

The power of the computational approaches of the notional scheme may be used to systematically develop an exhaustive list of all possible combinations of the polysaccharide sequences. For instance, an unconstrained combinatorial list of possible sequences of size $m^n$, where m is the number of building blocks and n is the number of positions in the chain may be used. In FIG. 4C, there are 256 different saccharide combinations that are theoretically possible (4 combinations for each branch and 4 branches=$4^4$).

A mass line of the 256 different polysaccharide structures may be plotted. Then the rules of biosynthetic pathways may be used to further analyze the polysaccharide. In the example (shown in FIG. 4B), it is known that the first step of the biosynthetic pathway is the addition of GlcNac at the 1-3 linked chain (branch 1). Thus, branch 1 should be present for any of the other branches to exist. Based on this rule the 256 possible combinations may be reduced using a factorial approach to conclude that the branch 2, 3, and 4 exist if and only if branch one is non-zero. Similar constraints can be incorporated at the notation level before generation of the master list of ensembles. With the notation scheme in place, experimental data can be generated (such as MALDI-MS or CE or chromatography) and those sequences that do not satisfy this data can be eliminated. An iterative procedure therefore enables a rapid convergence to a solution.

Figure 4D:
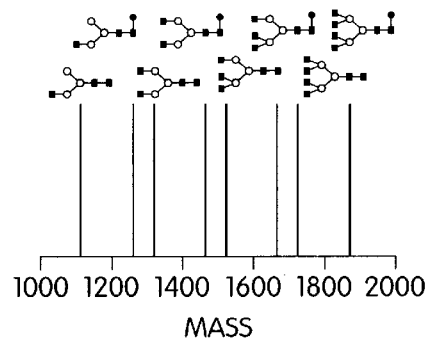

To identify branching patterns, a combination of MALDI-MS and CE (or other techniques) may be used, as shown in the Examples. Elimination of the pendant arms of the branched polysaccharide may be achieved by the judicious use of exo and endoenzymes. All antennary groups may be removed, retaining only the GlcNAc moieties extending from the mannose core and forming an "extended" core. In this way, information about branching is retained, but separation and identification of glycoforms is made simpler. One methodology that could be employed to form extended cores for most polysaccharide structures is the following. Addition of sialidases, and fucosidases will remove capping and branching groups from the arms. Then application of endo-β-galactosidase will cleave the arms to the extended core. For more unusual structures, other exoglycosidases are available, for instance xylases and glucosidases. By addition of a cocktail of degradation enzymes, any polysaccharide motif may be reduced to its corresponding "extended" core. Identification of "extended" core structures will be made by mass spectral analysis. There are unique mass signatures associated with an extended core motif depending on the number of pendant arms (FIG. 4D). FIG. 4D shows a massline of the "extended" core motifs generated upon exhaustive digest of glycan structures by the enzyme cocktail. Shown are the expected masses of mono-, di-, tri- and tetrantennary structures both with and without a fucose linked $\alpha 1 \rightarrow 6$ to the core GlcNAc moiety (from left to right). All of the "extended" core structures have a unique mass signature that is easily resolved by MALDI MS (from left to right). Quantification of the various glycan cores present may be completed by capillary electrophoresis, which has proven to be a highly rapid and sensitive means for quantifying polysaccharide structures. [Kakehi, K. and S. Honda, *Analysis of glycoproteins, glycopeptides and glycoprotein-derived polysaccharides by high-performance capillary electrophoresis*. J Chromatogr A, 1996. 720(1–2): p. 377–93.]

EXAMPLES

Example 1

Identification of the Number of Fragments Versus the Fragment Mass for Di, Tetra, and Hexasaccharide The masses of all the possible disaccharide, tetrasaccharide and hexasaccharide fragments were calculated and are shown in the mass line shown in FIG. 5. The X axis shows the different possible masses of the di, tetra and hexasaccharides and the Y axis shows the number of fragments that having that particular mass. Although there is a considerable overlap between the tetra and hexasaccharide the minimum difference in their masses is 13.03 D. Note that the Y axis has been broken to omit values between 17 and 40, to show all the bars clearly.

Example 2

Sequencing of an Octasaccharide of HLGAG

Using hepI, hepII, hepIII, nitrous acid, and exoenzymes, such as 2-sulfatase and α-iduronidase, β-glucuronidase, n-deacetylase as experimental constraints and the computer algorithm described above, an octasaccharide (O2), two decasaccharide (FGF binding and ATIII binding) and a hexasaccharide sequence of HLGAG were sequenced.

1. Compositional Analysis of O2

Compositional analysis of O2 was completed by exhaustive digest of a 30 μM sample with heparinases I–III and analysis by capillary electrophoresis (CE). Briefly, to 10 μL of polysaccharide was added 200 nM of heparinases I–III in sodium phosphate buffer pH 7.0. The reaction was allowed to proceed at 30° C. overnight. For CE analysis the sample was brought to 25 μL. Naphthalene trisulfonic acid (2 μM) was run as an internal standard. Assignments of $\Delta U_{2S}$-$H_{NS,6S}$ and $\Delta U$-$H_{NS,6S}$ were made on the basis that they comigrated with known standards. The internal standard migrated between 4 and 6 mins, the trisulfated disaccharide $\Delta U_{2S}$-$H_{NS,6S}$ migrated between 6 and 8 mins and the disulfated disaccharide $\Delta U$-$H_{NS,6S}$ migrated between 8 and 10 mins. Integration of the peaks indicated that the relative amounts of the two saccharides was 3:1.

The CE data for O2 octasaccharide demonstrated that there is a major peak corresponding to the commonly occurring trisulfated disaccharide ($\Delta U_{2S}$-$H_{NS,6S}$) and a small peak that corresponds to a disulfated disaccharide ($\Delta U$-$H_{NS,6S}$). The relative abundance of these disaccharide units obtained from the CE data shows that there are 3 Ds (±) and a 5 (±). The number of possible combination of sequences having these disaccharide units is 32. The possible combinations are shown in Table 4 below.

| Possible sequences: | | | | |
|---|---|---|---|---|
| ±DDD5 | ±D5DD | ±5DDD | ±D-DD-5 | ±5DD-D |
| ±D-DD-5 | ±5DDD-D | ±D-5DD | ±D-D-D5 | ±5D-DD |
| ±DD-D5 | ±D5D-D | ±D-5D-D | ±DD5D | ±D5-DD |
| ±DD-5D | ±D-5-DD | ±D5-D-D | ±DD-5-D | ±D-5-D-D |
| ±D-D-D-5 | ±5D-D-D | ±D-D5D | ±5-DDD | ±5-DD-D |
| ±D-D5D | ±5-D-DD | | | |

(i) Heparinase 1 digest ↓

-continued

| Seq | Fragments formed | | |
|---|---|---|---|
| | (577) | (577) | (1074) |
| ±DDD5 | ±D | ±D | ±D5 |
| ±DDD-5 | ±D | ±D | ±D-5 |
| ±DD5D | ±D | ±D | ±D5 |
| ±DD-5D | ±D | ±D | ±D5 |

(ii) →

Heparinase III digest (iii)

| Seq | Fragments formed (1732) | |
|---|---|---|
| ±DDD5 | ±DDD | ±5 |

2. Digestion of O2 with Heparinase I

Digestion of O2 was completed using both a short procedure and an exhaustive digest. "Short" digestion was defined as using 100 nM of heparinase I and a digestion time of 10 minutes. "Exhaustive" digestion was defined as overnight digestion with 200 nM enzyme. All digests were completed at room temperature. In the case of O2, both digest conditions yield the same results. Short digestion with heparinase I yields a pentasulfated tetrasaccharide (no acetyl groups) of m/z 5300.1 (1074.6) and a disaccharide of m/z 4802.6 (577.1) corresponding to a trisulfated disaccharide. This profile did not change upon exhaustive digest of O2.

Upon treatment with heparinase I, O2 is clipped to form fragments with m/z 4802.6 and 5,300.1. From the masses of these fragments it was possible to uniquely determine that m/z of 4802.6 corresponded to a trisulfated disaccharide and m/z of 5300.1 corresponded to a pentasulfated tetrasaccharide. Since the disaccharide composition of the sequence was known the only trisulfated disaccharide that may be formed is ±D and the possible pentasulfated tetrasaccharides that may be formed are ±5D, ±5-D, ±D5 and ±D-5. After identification of the fragments, the next step was to arrange them to give the right sequence. Since this was a cumbersome job to be handled manually a computer simulation was used to progressively eliminate sequences from the master list that did not fit the experimental data. Using the rule that heparinase-I cleaves before and $I_{2S}$ the heparinase-I digestion was simulated on the computer to generate the fragments for all the 32 sequences in the master list. From the list of fragments formed for each sequence, the computer was used to search for fragments that corresponded to the di and tetrasaccharide observed from the mass spectrometry data. The sequences that gave the fragments that fit the mass spec data of hep I are shown in FIG. 5a. It may be observed from FIG. 5a that all the sequences have 3 Ds which is consistent with the known rules for hepI digestion used to produce these fragments. It may also be observed that two arrangements give the same product profile namely having the +/−5 (I-$H_{NAc,6S}$ or G-$H_{NS,6S}$) the reducing end and having +/−5 at the second position from the non-reducing end. To resolve this issue a second experimental constraint, digestion with hepIII, was used.

Table 4 provides a list of sequences that satisfy the product profiles of hepI and hepIII digests of the octasaccharide O2. (a) shows the sequences that gave the di and tetrasaccharide fragments as observed from the mass spectrometry data. The fragments listed below along with their masses are those generated by computer simulation of hepI digest. (b) sequences in (a) that give the hexasaccharide fragment observed in the mass spectrometry data after hepIII digestion. The fragments along with their masses were generated by computer simulation of hepIII digestion.

3. Digestion of O2 with Heparinase III

Digestion of O2 with heparinase III yielded a nonasulfated hexasaccharide of m/z 5958.7 (1731.9) and an unobserved disulfated disaccharide (to conserve sulfates). Both short and exhaustive digests yielded the same profile.

Heparinase III treatment of O2 resulted in a major fragment of m/z 5958.7 which was uniquely identified as a hexasaccharide with 9 sulfate groups. The only sequence that satisfied the product profile of hepIII digestion was ±DDD−5 which is shown in Table 4. Table 4 shows that there should be a −5 (G-$H_{NAc,6S}$) in the reducing end. This was consistent with the rule used for hepIII digestion, i.e. hepIII clips before a G. The masses shown in the table are integers. The masses used to search for the required fragments were accurate to two decimal places.

Thus it was possible to demonstrate the ability to converge to the final sequence starting from the list of all possible sequences by eliminating sequences that do not fit experimental data. Since the starting point was a list of all the possible sequences given the composition of a sequence it was not possible that any sequences were missed during the analysis.

Example 3

Sequencing of a Basic Fibroblast Growth Factor (FGF-2) Binding Saccharide

MALDI-MS of a basic fibroblast growth factor (FGF-2) binding saccharide was performed to determine the mass and size of the saccharide as a complex with FGF-2 (G. Venkataraman et al., PNAS. 96, 1892, (1999)). Dimers of FGF-2 bound to the saccharide (S) yielding a species with a m/z of 37,009. By subtraction of FGF-2 molecular weight, the molecular mass of the saccharide was determined to be 2808, corresponding to a decasaccharide with 14 sulfates and an anhydromannitol at the reducing end.

1. Compositional Analysis

Compositional analysis and CE of FGF-2 binding saccharide were completed as described above. Compositional analysis of this sample resulted in two peaks corresponding to ±D ($\Delta U_{2S}H_{NS,6S}$) and ±D' ($\Delta U_{2S}Man_{6S}$) in the ratio 3:1. As this decasaccharide was derived by nitrous acid degradation of heparin, the uronic acid at the non-reducing end was not observed by CE (232 nm). Therefore, the non-reducing end residue was identified as +D ($I_{2S}H_{NS,6S}$) by sequencing with exoenzymes. The number of possible sequences with this composition is 16 Table 5(i). Of the 16 sequences, those that could result in the observed fragments upon heparinase I digestion of the decasaccharide are shown in Table 5(ii).

(i)

| Possible sequences | |
|---|---|
| 1. ±DDDDD' | 9. ±D-DDDD' |
| 2. ±DDDD-D' | 10. ±D-DDD-D' |
| 3. ±DDD-DD' | 11. ±D-DD-DD' |
| 4. ±DDD-D-D' | 12. ±D-DD-D-D' |
| 5. ±DD-DDD' | 13. ±D-D-DDD' |
| 6. ±DD-DD-D' | 14. ±D-D-DD-D' |
| 7. ±DD-D-DD' | 15. ±D-D-D-DD' |
| 8. ±DD-D-D-D' | 16. ±D-D-D-D-D' |

(ii)

| Sequence | Fragments formed | | | |
|---|---|---|---|---|
| | (577) | (577) | (577) | (1059) |
| ±DDDDD' | ±D | ±D | ±D | ±DD' |
| ±DDDD-D' | ±D | ±D | ±D | ±D-D' |

(iii)

| Sequence | Fragments formed | | | |
|---|---|---|---|---|
| | (577) | (577) | (577) | (577) |
| ±DDDDD' | ±D | ±D | ±D | ±D' |

2. Digestion with Heparinase I and Heparinase III

To resolve the isomeric state of the internal uronic acid +D vs. −D, exhaustive digestion of the saccharide with heparinase I and heparinase III was performed. Heparinase I exhaustive digestion of the saccharide results in only two species corresponding to a trisulfated disaccharide(±D) and its anhydromannitol derivative, while heparinase III did not cleave the decasaccharide at all.

Heparinase I digestion of the decasaccharide yielded a pentasulfated tetrasaccharide (m/z 5286.3) with an anhydromannitol at the reducing end and a trisulfated disaccharide of m/z 4804.6. Table 5 shows the convergence of the FGF binding decasaccharide sequence. Thus, it provides a list of sequences that satisfied the mass spectrometry product profiles of FGF-2 binding saccharide on treatment with hepI. Section (i) of Table 5 shows the master list of 16 sequences derived from compositional analysis and exoenzyme sequencing of the non-reducing end. The disaccharide unit at the non-reducing end was assigned to be a +D using exoenzymes and the anhydromannitol group at the reducing end is shown as '. The mass of the fragments resulting from digestion of decasaccharide with heparinase I are shown in (ii). Also shown in (ii) are those sequences from (i) that satisfy heparinase I digestion data. Section (iii) of Table 5 shows the sequence of decasaccharide from (ii) that satisfies the data from exhaustive digestion using heparinase I. This product profile may be obtained only if there is a hepI cleavable site at every position in the decasaccharide which led us to converge to the final sequence DDDDD' shown in section iii of Table 5. The above taken together confirm the sequence of the FGF-2 binding decasaccharide sequence to be DDDDD' $[(I_{2S}H_{NS,6S})_4I_{2S}Man_{6S}]$.

Example 4
Sequencing of an AT-III Binding Saccharide

An AT-III binding saccharide was used as an example of the determination of a complex sequence.

1. Compositional Analysis

Compositional analysis and CE were completed as described above. Compositional analysis of an AT-III binding saccharide indicated the presence of three building blocks, corresponding to $\Delta U_{2S}H_{NS,6S}$ (±D), $\Delta UH_{NAc,6S}$ (±4) and $\Delta UH_{NS,3S,6S}$ (±7) in the relative ratio 3:1:1 respectively. The shortest polysaccharide that may be formed with this composition corresponds to a decasaccharide, consistent with the MALDI-MS data. The total number of possible combinations of this tridecasulfated single acetylated decasaccharide sequences with the above disaccharide building blocks is 320 Table 6.

(iii)

```
320
 |
(i)
 |
52
 |
(ii)
 |
28
```

| Sequence | Fragments formed and their mass | | | | |
|---|---|---|---|---|---|
| | 577 | 1037 | 1731 | 1093 | 1670 |
| ±DDD47$^t$ | ±D | ±D4 | ±DDD | ±47t | ±D47$^t$ |
| ±DDD-47$^t$ | ±D | ±D-4 | ±DDD | ±47t | ±D-47$^t$ |
| ±DDD4-7$^t$ | ±D | ±D4 | ±DDD | ±4-7t | ±D4-7$^t$ |
| ±DDD-4-7$^t$ | ±D | ±D-4 | ±DDD | ±4-7t | ±D-4-7$^t$ |
| ±7DD4-Dt | ±7/±D | ±D4 | ±7DD | ±4-Dt | ±D4-D$^t$ |
| ±7DD-4-Dt | ±7/±D | ±D-4 | ±7DD | ±4-Dt | ±D-4-D$^t$ |

2. Digestion with Heparinase I

Digestion of this decasaccharide with heparinase I resulted in four fragments. The major fragments include a decasulfated singly-acetylated octasaccharide (m/z 6419.7), a heptasulfated, singly acetylated hexasaccharide with m/z 5842.1, a hexasulfated tetrasaccharide with m/z of 5383.1 and a trisulfated disaccharide (m/z 4805.3). Also present is a contaminant (*), a pentasulfated tetrasaccharide. The sequence of AT-III binding decasaccharide has been reported to be D4-7DD, on the basis of NMR spectroscopy (Y. Toida et al., J. Biol. Chem. 271, 32040 (1996)). Such a sequence should show the appearance of a tagged D or DD residue at the reducing end. However, we have found all the different experiments used in the elucidation of the decasaccharide sequence to be consistent with each other in the appearance of a 4–7 tagged product and not a D (or a DD) product. Surprisingly, this saccharide did not contain an intact AT-III binding site, as proposed. Therefore, confirmation of the proposed sequence was sought through the use of integral glycan sequencing (IGS) methodology. The result of IGS agreed with our analysis. A minor contaminant saccharide has also been found. Of the 320 possible sequences, only 52 sequences satisfied heparinase I digestion data Table 6(i). The mass spectrum of the exhaustive digestion of the decasaccharide with heparinase I showed m/z values that corresponded to a trisulfated disaccharide and a octasulfated hexasaccharide, thereby further reducing the list of 52 sequences to 28 sequences Table 6(ii).

3. Digestion with Heparinase II

To further converge on the sequence, a 'mass-tag' was used at the reducing end of the saccharide (Δ m/z of 56.1 shown as 't'). This enabled the identification of the saccharide sequence close to and at the reducing end. Typical yields for the mass-tag labeling varied between 80–90% as determined by CE. Treatment of the semicarbazide tagged decasaccharide, with heparinase II resulted in the following products: m/z 5958.4 (nine sulfated hexasaccharide), m/z 5897.7 (tagged heptasulfated, singly acetylated hexasaccharide), m/z 5380.1 (hexasulfated tetrasaccharide), m/z 5320.9 (tagged tetrasaulfated tetrasaccharide), m/z 5264.6 (tetrasulfated tetrasaccharide) and m/z 4805.0 (a trisulfated disaccharide). The m/z value of 5320.9 and 5897.7 corresponded to a tagged tetrasulfated tetrasaccharide and a tagged heptasulfated hexasaccharide, both containing the N-acetyl glucosamine residue. This result indicated that +/−4 ($I/GH_{NAc,6S}$) is present at the reducing or one unit from the reducing end, thereby limiting the number of possible sequences from 28 to 6 Table 6(iii).

4. Digestion with Nitrous Acid

Partial nitrous acid digestion of the tagged as well as the untagged decasaccharide provided no additional constraints but confirmed the heparinase II data. Exhaustive nitrous acid digestion, however, gave only the reducing end tetrasaccharide (with and without the tag) as an unclipped product. Exhaustive nitrous acid treatment of decasaccharide essentially gives one tetrasulfated single-acetylated anhydromannitol tetrasaccharide species (one tagged m/z 5241.5 and one untagged m/z 5186.5). This confirmed that +/−4 ($I/GH_{NAc, 6S}$) is one unit away from the reducing end. Sequential use of exoenzymes uniquely resolved the isomeric state of the uronic acid as +4 and the reducing end disaccharide to be −7 consistent with 4–7 being the key AT-III binding motif. Treatment of this tetrasaccharide with iduronidase (and not glucuronidase) resulted in a species of m/z 5007.8 corresponding to the removal of iduronate residue. Further treatment with exoenzymes only in the following order (glucosamine 6-O sulfatase, hexosamidase and glucuronidase) resulted in the complete digestion of the trisaccharide. Table 6 shows the convergence of the AT-III binding decasaccharide sequence from 320 possible sequences to 52 to 28 to 6 to the final sequence. Thus, the sequence of the AT-III binding decasaccharide was deduced as ±DDD4−7 ($\Delta U_{2S}H_{NS,6S}I_{2S}H_{NS,6S}I_{2S}H_{NS,6S}IH_{NAc,6S}GH_{NS, 3S,6S}$).

Example 5

Sequencing of a Hexasaccharidel of HLGAG 10 pM H1 was treated with 2 mM nitrous acid in 20 mM HCl at room temperature for 20 minutes such that limited degradation occurred. After 20 minutes, a two-fold molar excess of (arg-gly)$_{19}$arg in saturated matrix solution was added. 1 pmol of saccharide was spotted and used for mass spectrometric study. All saccharides were detected as noncovalent complexes with (arg-gly)$_{19}$arg. Starting hexasaccharide was observed as was a tetrasaccharide and disaccharide. Also observed is uncomplexed peptide (not shown in figures). Hereafter two m/z values are reported. The first is the observed m/z value that corresponds to the saccharide+peptide. The second number in parentheses is the m/z of the saccharide alone obtained by subtracting the mass of the peptide.

After 20 minutes, nitrous acid treatment of H1 yielded starting material at m/z 5882.5 (1655.8) which corresponded to a hexasaccharide with 8 sulfates and an anhydromannitol at the reducing end, a m/z 5304.1 (1077.3), which corresponded to a tetrasaccharide with the anhydromannitol at the reducing end and a m/z of 4726.2 (499.4) which corresponded to a disulfated disaccharide with the anhydromanitol at the reducing end.

This sample was then subjected to exoenzyme analysis. Three exoenzymes were added—iduronate 2-O sulfatase, iduronidase, and glucosamine 6-O sulfatase. The nitrous acid sample was neutralized via addition of 1/5 volume of 200 mM sodium acetate 1 mg/mL BSA pH 6.0 after which the enzymes were added. Glucosamine 6-O sulfatase was added after digestion with the first two enzymes was complete. Final enzyme concentrations were in the range of 20–40 milliunits/mL and digestion was carried out at 37° C. for a minimum of two hours.

Upon incubation with iduronate 2-O sulfatase and iduronidase, the hexasaccharide and tetrasaccharide peaks were reduced in mass. The disaccharide was no longer detectable after incubation with the enzymes. The hexasaccharide gave a new species at m/z 5627.3 (1398.8) corresponding to loss of sulfate and iduronate. The tetrasaccharide yielded a species of m/z 5049.3 (820.8) again corresponding to loss of sulfate at the 2-O position and loss of iduronate. These data showed that all the disaccharide building blocks contained an I2S.

Addition of glucosamine 6-O sulfatase and incubation overnight at 37° C. resulted in the production of two new species. One at m/z 5546.8 (1318.3) resulting from loss of sulfate at the 6 position on glucosamine and the other at m/z 5224.7 (996.2), again corresponding to a tetrasaccharide 6-O sulfate. These data showed that except for the reducing end anhydromanitol containing disaccharide unit the other units contained HNS. The data indicated that the sequence is DDD', indicating that this sequence was originally derived from nitrous acid degradation unlike the other sequences which were derived from degradation by the heparinases.

Example 6

Sequencing of Other Complex Polysaccharides

The sequencing approach may be readily extended to other complex polysaccharides by developing appropriate experimental constraints. For example, the dermatan/chondroitin mucopolysaccharides (DCMP) consisting of a disaccharide repeat unit is amenable to a hexadecimal coding system and MALDI-MS. Similar to what is observed for HLGAGs, there is unique signature associated with length and composition to a given mass in DCMP. For instance, the minimum difference between any disaccharide and any tetrasaccharide is 139.2 Da, therefore, the length, the number of sulfates and acetates may be readily assigned for a given DCM polysaccharide up to an octa-decasaccharide. Similarly, in the case of polysialic acids (PSA), present mostly as homopolymers of 5-N-acetylneuraminic acid (NAN) or 5-N-glycolylneuraminic acid (NGN), the hexadecimal coding system may be easily extended to NAN/NGN to encode the variations in the functional groups and enabling a sequencing approach for PSA.

1. Dermatan/Chondroitin Family of Complex Mucopolysaccharides

DCMP are found in dense connective tissues such as bone and cartilage. The basic repeat unit of the dermatan/chondroitin mucopolysaccharides (DCMP) may be represented as $-(\beta 1 \rightarrow 4)U_{2X}-(\alpha/\beta 1 \rightarrow 3)Gal_{NAc, 4X, 6X}$, where U is uronic acid, $Gal_{NAc}$ is a N-acetylated galactosamine. The uronic acid may be glucuronic acid (G) or iduronic acid (I)

and sulfated at the 2-O position and the galactosamine (GalNAc) may be sulfated in the 4-O or the 6-O position, thereby resulting in 16 possible combinations or building blocks for DCMP. Like the heparinases that degrade HLGAGs, there are distinct chondoroitinases and other chemical methods available that clip at specific glycosidic linkages of DCMP and serve as experimental constraints. Furthermore, since DCMPs are acidic polysaccharides, the MALDI-MS techniques and methods used for HLGAGs may be readily extended to the DCMPs.

PEN scheme and mass-identity relationships for DCMP: Shown in Table 7 are the property-encoded nomenclature (PEN) of the 16 possible building blocks of dermatan/chondroitin family of molecules. The sequencing approach enables one to establish important mass-identity relationships as well as master list of all possible DCMP sequences from disaccharides to dodecasaccharides. These are plotted as a mass line as shown in FIG. 5. As observed for HLGAGs, there is a unique signature associated with length and composition for a given mass. As described above the minimum difference between any disaccharide and any tetrasaccharide was found to be 101 Daltons for HLGAGs. Interestingly, in the case of DCMP the minimum difference between any disaccharide and any tetrasaccharide is 139.2 Da. Therefore, the length, the number of sulfates and acetates may be readily assigned for a given DCM polysaccharide up to an octa-decasaccharide.

TABLE 7

| I/G | 2X | 6X | 4X | ALPH CODE | DISACC | MASS (ΔU) |
|---|---|---|---|---|---|---|
| 0 | 0 | 0 | 0 | 0 | I-Gal$_{NAc}$ | 379.33 |
| 0 | 0 | 0 | 1 | 1 | I-Gal$_{NAc,4S}$ | 459.39 |
| 0 | 0 | 1 | 0 | 2 | I-Gal$_{NAc,6S}$ | 459.39 |
| 0 | 0 | 1 | 1 | 3 | I-Gal$_{NAc,4S,6S}$ | 539.45 |
| 0 | 1 | 0 | 0 | 4 | I$_{2S}$-Gal$_{NAc}$ | 459.39 |
| 0 | 1 | 0 | 1 | 5 | I$_{2S}$-Gal$_{NAc,4S}$ | 539.45 |
| 0 | 1 | 1 | 0 | 6 | I$_{2S}$-Gal$_{NAc,6S}$ | 539.45 |
| 0 | 1 | 1 | 1 | 7 | I$_{2S}$-Gal$_{NAc,4S,6S}$ | 619.51 |
| 1 | 0 | 0 | 0 | -0 | G-Gal$_{NAc}$ | 379.33 |
| 1 | 0 | 0 | 1 | -1 | G-Gal$_{NAc,4S}$ | 459.39 |
| 1 | 0 | 1 | 0 | -2 | G-Gal$_{NAc,6S}$ | 459.39 |
| 1 | 0 | 1 | 1 | -3 | G-Gal$_{NAc,4S,6S}$ | 539.45 |
| 1 | 1 | 0 | 0 | -4 | G$_{2S}$-Gal$_{NAc}$ | 459.39 |
| 1 | 1 | 0 | 1 | -5 | G$_{2S}$-Gal$_{NAc,4S}$ | 539.45 |
| 1 | 1 | 1 | 0 | -6 | G$_{2S}$-Gal$_{NAc,6S}$ | 539.45 |
| 1 | 1 | 1 | 1 | -7 | G$_{2S}$-Gal$_{NAc,4S,6S}$ | 619.51 | code for the substitution at the 4 and 6 position of the galactosamine. Column 5 shows the numeric code for the disaccharide unit, column 6 shows the disaccharide unit and column 7 shows the theoretical mass calculated for the disaccharide unit.

Tools as experimental constraints: Similar to the heparinases that degrade HLGAGs there are chondroitinases that degrade chondroitin-like and dermatan-like regions of DCMP. The chondroitinases B, C, AC and ABC have distinct specificities with some overlap. For the most part the chondroitinases cover the entire range of linkages found in DCMP. There are several chondroitinases that have been isolated and cloned from different sources. In addition to the enzymes, there are a few well-established chemical methods that may be used to investigate DCMP. These include nitrous acid treatment. Thus there are adequate tools (enzymatic and chemical) which function as 'experimental constraints' to enable DCMP sequencing. Below we use two DCMP sequences to illustrate sequencing DCMP.

A. Serpin HCF-2 Binding DCMP Hexasaccharide)

The minimum size DCMP binding to serpin HCF-2 was isolated and its composition was determined using elaborate methods which included anion exchange chromatography, paper electrophoresis and paper chromatography. The sequencing strategy through the integration of PEN and MS established the identity of this serpin HCF-2 binding saccharide to be a hexasaccharide with 6 sulfates and 3 acetates. The high degree of sulfation pointed to a dermatan-like saccharide. Since this saccharide was derived using partial N-deacetylation and nitrous acid treatment, it comprises a 5 membered anhydrotalitol ring at the reducing end. Composition analysis of the saccharide may be obtained by degradation using the chondroitinases. The composition shows the presence of $\Delta U_{2S}Gal_{NAc,4S}$ (±5) and $\Delta U_{2S}aTal_{4S}$ (aTal–anhydrotalitol–±5') in a 2:1 ratio. This enabled the generation of a master list with 8 possible sequences as shown in Table 8a. 2-sulfatase and iduronidase treatment of the hexasaccharide produced a shift in the mass spectrum corresponding to the loss of a sulfate and iduronate, thereby fixing the $I_{2S}$ at non-reducing end (Table 8b). In order to converge further, Chondroitinase B (which acts on iduronate residues in dermatan-like regions) was used and a single peak in the mass spectrum corresponding to a 2-sulfated disaccharide was observed. This led us to converge to the sequence +555' ($I_{2S}$-Gal$_{NAc,4S}$-$I_{2S}$-aTal$_{4S}$).

TABLE 8

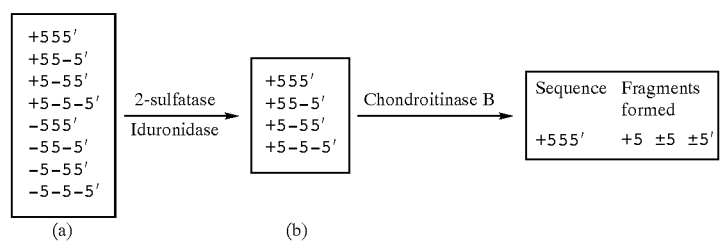

(a)      (b)

Table 7 shows the Property Encoding Numerical scheme used to code DCMPs. The first column codes for the isomeric state of the uronic acid (0 corresponding to iduronic and 1 corresponding to glucuronic). The second column codes for the substitution at the 2-O position of the uronic acid (0-unsulfated, 1-sulfated) . Columns 3 and 4

B. Hypothetical

Figure 6A:
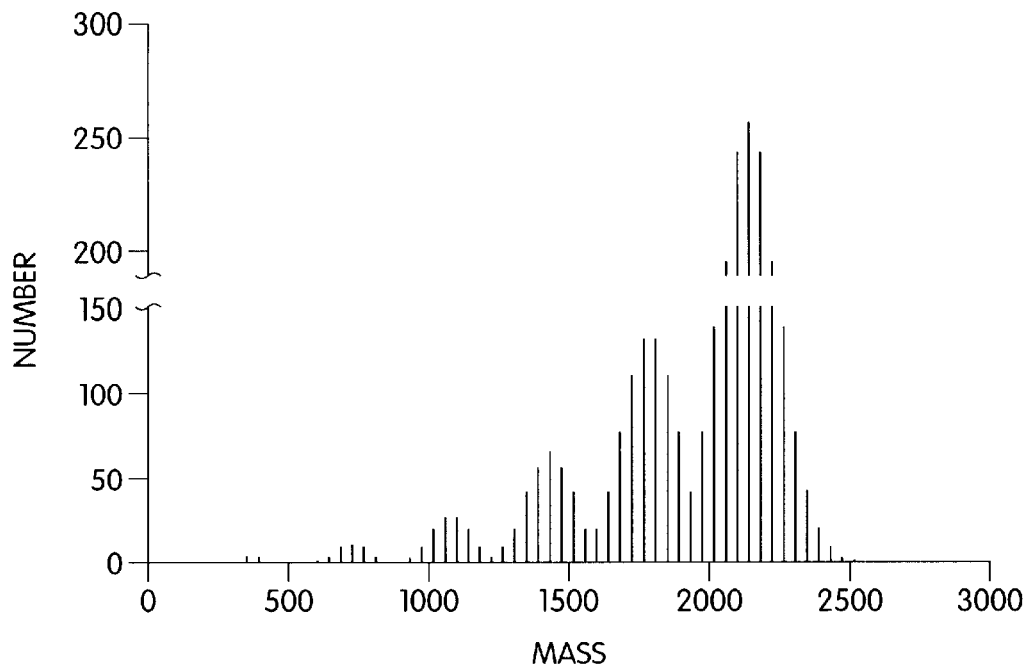
FIG. 6 is a mass-line diagram for (A) Polysialic Acid with NAN and (B) Polysialic Acid with NGN.

In this example a "hypothetical DCMP polysaccharide" which is more complex than the previous example is used. Assume that MS yields a result that is interpreted to be an octasaccharide with 8 sulfates and 4 acetates, and that the composition analysis points to three species corresponding to $\Delta U_{2S}Gal_{NAc,4S}$ (±5), $\Delta UGal_{NAC,6S}$ (±2) and $\Delta U_{2S}Gal_{NAc,4S,6S}$ (±7) in 2:1:1 relative abundance. This enables one to generate a master-list, which would point to 96 possible sequences (Table 9a). It is expected that the digestion of the saccharide sample with chondroitinase AC would result in two products with masses that would correspond to two tetrasulfated tetrasaccharide units and thereby reduce the master list to 4 possible sequences (Table 9b). Complete deamination using hydrazonolysis and nitrous acid treatment would result in 3 peaks, two corresponding to a disulfated disaccharide and the third corresponding to a trisulfated disaccharide. Treatment of the degraded products with 2-sulfatase and iduronidase (and not glucuronidase) should result in peaks that correspond to the loss of sulfate and iduronate residues. This would enable the identification of the isomeric state of 5 and 7 thereby converging the master-list to one sequence ±55–27 ($\Delta U_{2S}$-$Gal_{NAc,4S}$-$I_{2S}$-$Gal_{NAc,4S}$-G-$Gal_{NAc,6S}$-$I_{2S}$-$Gal_{NAc,4S,6S}$).

monomeric units for NAN and NGN. The mass-line for polymeric units of NGN are shown in FIGS. 6A and B. Note that there is a considerable overlap in masses observed for the higher order oligomers of both NAN and NGN (FIGS. 6A and B). The minimum difference in the masses between a n 'mer and a n+1 'mer stabilizes at 3.01 Da for NAN and 13 Da for NGN, as we go to tetra, penta and hexasaccharide, thereby providing a safe margin for detection of these fragments using MS.

TABLE 10

| NAN/NGN | 9X | 7X | 4X | Code | Saccharide unit | Mass |
|---|---|---|---|---|---|---|
| 0 | 0 | 0 | 0 | 0 | NAN | 309.28 |
| 0 | 0 | 0 | 1 | 1 | $NAN_{4Ac}$ | 351.32 |
| 0 | 0 | 1 | 0 | 2 | $NAN_{7Ac}$ | 351.32 |
| 0 | 0 | 1 | 1 | 3 | $NAN_{4Ac,7Ac}$ | 393.36 |

TABLE 9

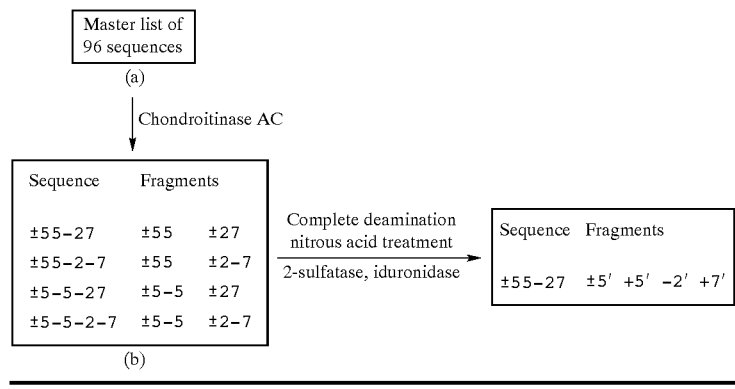

(a) Master list of 96 sequences → Chondroitinase AC (b)
| Sequence | Fragments |
|---|---|
| ±55–27 | ±55  ±27 |
| ±55–2–7 | ±55  ±2–7 |
| ±5–5–27 | ±5–5  ±27 |
| ±5–5–2–7 | ±5–5  ±2–7 |

Complete deamination nitrous acid treatment / 2-sulfatase, iduronidase →

| Sequence | Fragments |
|---|---|
| ±55–27 | ±5' +5' −2' +7' |

It is important to reiterate that, similar to what was developed for HLGAG, distinct or additional 'convergence strategies or experimental constraints' may be used to arrive at the 'unique' solution for DCMP.

2. Polysialic Acid

Polysialic acids are linear complex polysaccharides found as a highly regulated post-translational modification of the neural cell adhesion molecule in mammals that are present mostly as homopolymers of 5-N-acetylneuraminic acid (NAN) or 5-N-glycolylneuraminic acid (NGN). The monomeric units of NAN and NGN are linked by α2–8 glycosidic linkages, and may be modified at the 4-O, 7-O, and 9-O positions. The major modification is acetylation. In addition, much rarer modifications including sulfation and lactonization occur at the 9-O position. A deaminated form of neuraminic acid namely 5-deamino-3,5-dideoxyneuraminic acid (KDN) has also been discovered. The PEN-MS sequencing approach is extended to polysialic acids, and using NAN and NGN units we illustrate how this is achieved.

PEN scheme and mass-identity relationships for PSA. PSA is comprised of two different monomeric repeats, with variations in the modification of each unit. The flexibility of the PEN enables easy adaptation to a monomeric repeat unit for PSA from the dimeric repeats for HLGAG and DCMP. The PEN scheme for PSA is shown in Table 10. The sequencing approach establishes important mass-identity relationships as well as master list of all the combinations of TABLE 10-continued

| NAN/NGN | 9X | 7X | 4X | Code | Saccharide unit | Mass |
|---|---|---|---|---|---|---|
| 0 | 1 | 0 | 0 | 4 | $NAN_{9Ac}$ | 351.32 |
| 0 | 1 | 0 | 1 | 5 | $NAN_{4Ac,9Ac}$ | 393.36 |
| 0 | 1 | 1 | 0 | 6 | $NAN_{7Ac,9Ac}$ | 393.36 |
| 0 | 1 | 1 | 1 | 7 | $NAN_{4Ac,7Ac,9Ac}$ | 435.40 |
| 1 | 0 | 0 | 0 | -0 | NGN | 325.27 |
| 1 | 0 | 0 | 1 | -1 | $NGN_{4Ac}$ | 367.32 |
| 1 | 0 | 1 | 0 | -2 | $NGN_{7Ac}$ | 367.32 |
| 1 | 0 | 1 | 1 | -3 | $NGN_{4Ac,7Ac}$ | 409.36 |
| 1 | 1 | 0 | 0 | -4 | $NGN_{9Ac}$ | 367.32 |
| 1 | 1 | 0 | 1 | -5 | $NGN_{4Ac,9Ac}$ | 409.36 |
| 1 | 1 | 1 | 0 | -6 | $NGN_{7Ac,9Ac}$ | 409.36 |
| 1 | 1 | 1 | 1 | -7 | $NGN_{4Ac,7Ac,9Ac}$ | 451.40 |

Shown in Table 10 is the Property Encoded Numerical scheme for PSA. Column 1 codes for whether the monomeric unit is NAN or NGN. Columns 2,3 and 4 code for the variations in the 9, 7 and 4 positions respectively, where 1 corresponds to acetylated and 0 corresponds to unacetylated. Column 5 shows the numeric code for the PSAs. −0 to −7 was used instead of 8–F. Assigning the numbers to code for the variability in acetylation and the sign would indicate if it is NAN/NGN. Column 6 lists the monosaccharide represented by the code in column 5. Column 7 lists the theoretical mass calculated for the monomeric units shown in column 6.

The mass-line for the combinations of substituted/ unsubstituted NAN containing monomeric units in PSA is shown in FIG. 6A. The X-axis represents the calculated masses for monosaccharide to hexasaccharides. Shown in the Y axis is the number of fragments of a particular length and composition that exists for a given mass. The values 150–190 were omitted to improve the clarity of the other peaks. The minimum difference between any monosaccharide and any disaccharide is 165.2 Da, between any di and any trisaccharide is 39.03 Da, between any tri and any tetrasaccharide is 39.03 Da and 3.01 Da for all higher order saccharides.

Figure 6B:
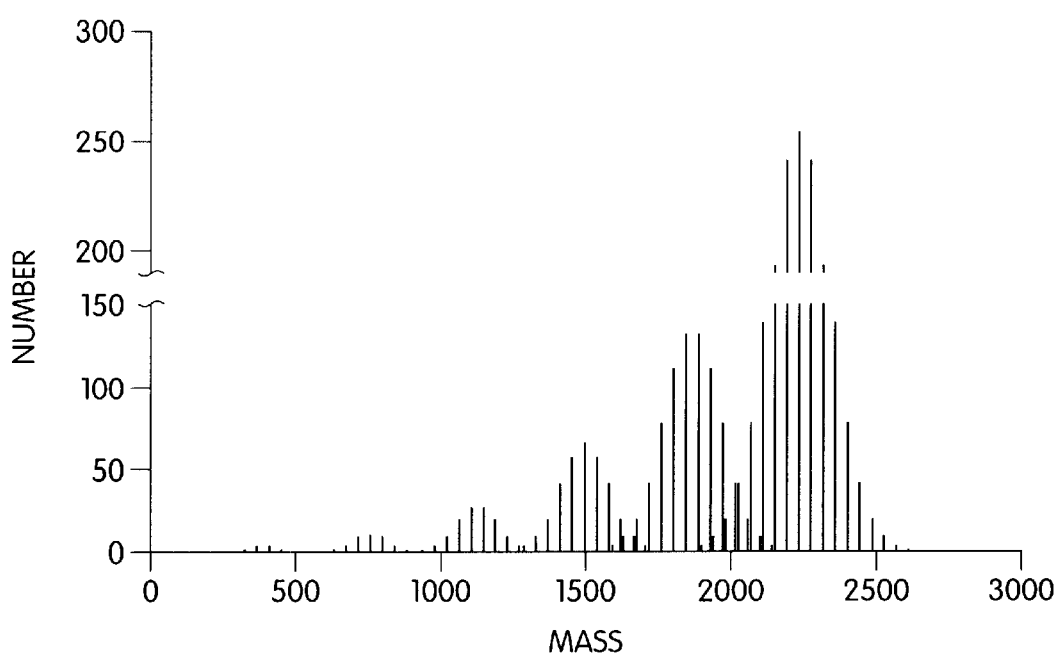

The mass-line for the combinations of substituted/ unsubstituted NGN monomeric units in PSA is shown in FIG. 6B. The X-axis represents the calculated masses for monosaccharide to hexasaccharide. Shown in the Y axis is the number of fragments of a particular length and composition that exist for a given mass. The values 150–190 were omitted to improve the clarity of the other peaks. The minimum difference between any monosaccharide and any disaccharide is 181.2 Da, between any di and any trisaccharide is 55.03 Da and 13 Da for higher order saccharides.

Tools as experimental constraints. There are several tools and detection methods available for studying PSAs. Based on the properties of the building blocks of PSA, this class of linear polysaccharides is amenable for MS. Methods of purifying PSA polymers and obtaining composition using HPLC, CE and mass spectrometry have very recently been established. Enzymatic tools from various sources have been used to study PSA extensively. Notably the bacterial exosalidase which cleave PSA polymers processively from the non-reducing end and the bacteriophage derived endoneuramidase, which clips endolytically both the NAN and NGN containing PSA linear polysaccharides. In addition to these enzymes chemical methods such as hydrozonolysis followed by nitrous acid treatment and periodate oxidation followed by sodium borohydrate treatment may be used to as tools to degrade PSA polysaccharides into smaller polysaccharides.

Example 7

Figure 7A:
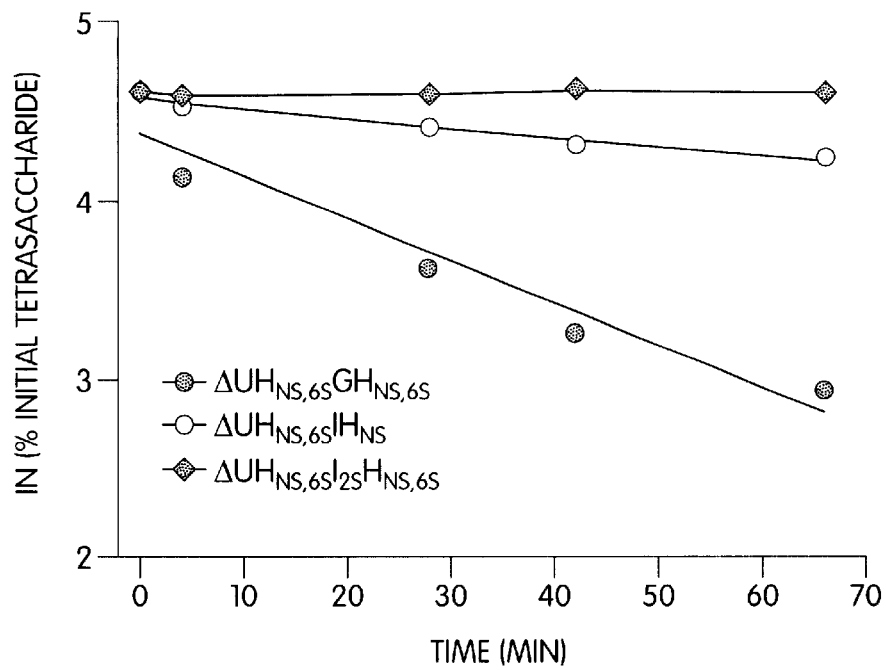
FIG. 7 is a graph (A) depicting cleavage by Hep III of either G( ) I(O) or $I_{2S}$( ) linkages, and a graph (B) depicting same study as in A but where cleavage was performed with Hep I.

Variation of Experimental Conditions Resulting in Alteration of Enzymatic Reactions and Its Effect on the Methods of the Invention Secondary specificities of the heparinases have been observed, especially under exhaustive degradation conditions. As a part of ongoing investigations into the enzymology of heparinases, the relative rates of cleavage of I and G containing sites by heparinase I and III with defined substrates under different conditions have been measured. For instance heparinase III cleaves both at I and G containing linkages and not $I_{2S}$ [H. E. Conrad, *Heparin Binding Proteins* (Academic Press, San Diego, 1998).]. However, under the reaction conditions used in this study, there is a dramatic (8–10 fold) difference in the rates of cleavage, with I-containing linkages being clipped more slowly than G-containing linkages (FIG. 7A). FIG. 7A shows cleavage by recombinant heparinase III of tetrasaccharides containing either G (●), I(○) or $I_{2S}$ (◆) linkages. Each reaction was followed by capillary electrophoresis. With these substrates, heparinase III does not cleave $I_{2S}$-containing glycosidic linkages, and cleaves G-containing linkages roughly 10 times as fast as I-containing linkages. Under the "short" conditions of digest it is expected that only G-containing saccharides are cleaved to an appreciable extent. [Conditions for enzymatic digest of HLGAG oligosaccharides were set forth above, briefly, Digests were either designated as "short" or "exhaustive". Short digests were completed with 50 nM enzyme for 10 minutes. Exhaustive digests were completed using 200 nM enzyme for either four hours or overnight. Partial nitrous acid cleavage was completed using a modification of published procedures. Briefly, to an aqueous solution of saccharide was added a 2×solution of sodium nitrite in HCl such that the concentration of nitrous acid was 2 mM and HCl was 20 mM. The reaction was allowed to proceed at room temperature with quenching of aliquots at various time points via the addition of 1 µL of 200 mM sodium acetate 1 mg/mL BSA pH 6.0. Exhaustive nitrous acid was completed by reacting saccharide with 4 mM nitrous acid in HCl overnight at room temperature. In both cases, it was found that the products of nitrous acid cleavage could be sampled directly by MALDI without further cleanup and without the need to reduce the anhydromannose residues to anhydromannitol. The entire panel of HLGAG degrading exoenzymes were purchased from Oxford Glycosystems (Wakefield, Mass.) and used as suggested by the manufacturer.] For example, with the hexasaccharide $\Delta UH_{NH,6S}GH_{NS}IH_{NAc}$, (which contains both I and G in a minimally sulfated region) cleavage occurs only at the G under "short" digest conditions as shown in Table II.

TABLE II

| Species | m/z (+ Peptide) | Observed |
| --- | --- | --- |
| $\Delta UH_{NH,6S}GH_{NS}IH_{Nac}$ | 5442.1 | ✓ |
| $\Delta UH_{NS}IH_{NAc}$ | 5023.6 | ✓ |
| $\Delta UH_{NH,6S}GH_{NS}$ | 5061.7 | |

Figure 7B:
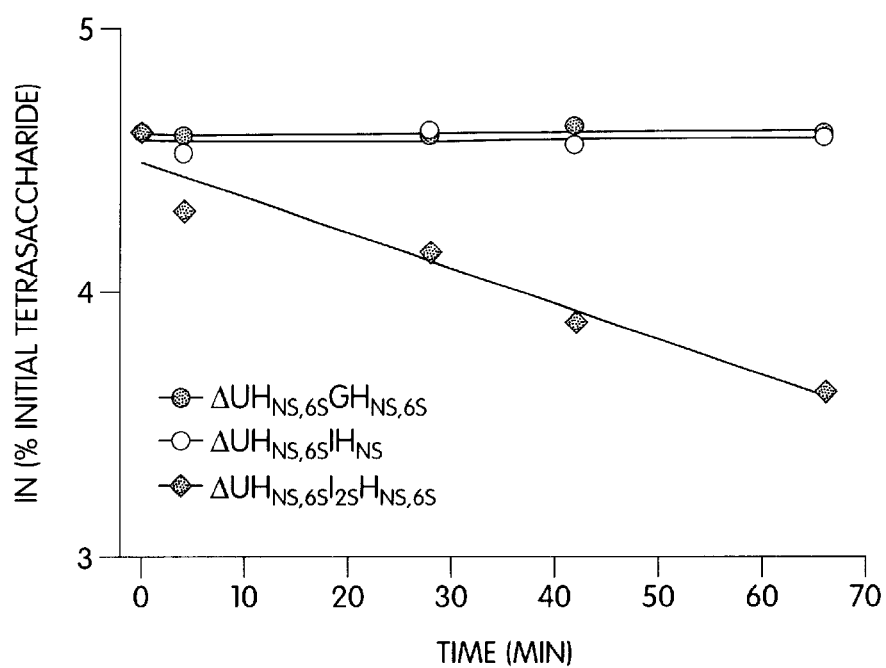

Heparinase II was incubated with the hexasaccharide $\Delta UH_{NH,6S}GH_{NS}IH_{Nac}$ and only cleavage at the G and not the I was observed. Furthermore, we have found that degree of sulfation does affect the kinetics of heparinase III degradation of oligosaccharides [S. Ernst et al., *Crit. Rev. Biochem. Mol. Biol.* 30, 387 (1995); S. Yamada et al., *Glycobiology* 4, 69 (1994); U. R. Desai, H. M. Wang, R. J. Linhardt, *Biochemistry* 32, 8140 (1993); R. J. Linhardt et al., *Biochemistry* 29, 2611 (1990).]. In the case of heparinase I, this enzyme does not clip either I or G-containing glycosidic linkages within the context of our experimental procedures, whereas it readily clips $I_{2S}$ containing polysaccharides (FIG. 7B). FIG. 7C shows the same study as completed in (A) except heparinase I was used instead of heparinase III. With heparinase I, cleavage only occurs at $I_{2S}$-containing linkages but not before I or G. There is only one report of heparinase I clipping $G_{2S}$ containing linkages [S. Yamada, T. Murakami, H. Tsuda, K. Yoshida, K. Sugahara, *J. Biol. Chem.* 270, 8696 (1995).], which was tested with two tetrasaccharide substrates and the experiments were performed under conditions which are kinetically very different from the 'short' heparinase I digestion presented here.

Quite a few factors have severely limited and complicated prior art studies and interpretation of heparinase substrate specificity experiments. First, not only is a homogenous substrate preparation difficult, but also analyzing the substrates and products have been very challenging. Analysis has primarily relied on co-migration of the saccharides with known standards, and as others and we have observed, oligosaccharides with different sulfation patterns do co-migrate, complicating unique assignments. Further, some oligosaccharides used in previous studies to assign substrate specificity for the heparinases were not homogeneous, complicating analysis. The development of the MALDI-MS procedure of the invention has enabled rapid and accurate determination of the saccharides. The second problem is the preparation of pure wild-type heparinases from the native host. The wild-type heparinase is isolated from *Flavobacterium heparinum* and this organism produces several complex polysaccharide-degrading enzymes, and often these copurify with each other. For example, when examining the kinetics of heparinase III, we found that a commercial source of heparinase III was able to degrade the supposedly non-cleavable $\Delta U_{2S}H_{NS,6S}I_{2S}H_{NS,6S}$. Furthermore, MS and CE analysis of the products indicated that one was specifically 2-O desulfated suggesting a sulfatase contamination. Recombinant heparinase III produced and purified in our laboratory (and not having contamination with other heparin degrading enzymes) does not cleave $\Delta U_{2S}H_{NS,6S}I_{2S}H_{NS,6S}$ as expected. Thus, different enzyme preparations and differences in digestion conditions, and differences in substrate size and composition and often contaminating substrates, taken together with assignments based on co-elution make comparison of data not only very difficult but also has led to contradictory findings.

Regardless of the outcome of heparinase substrate specificities, there are other methods that may be used to extract the isomeric state of the uronic acid [I or G or $I_{2S}$ or $G_{2S}$]. The uronic acid component of each disaccharide unit may be unambiguously ascertained by completing compositional analysis after exhaustive nitrous acid treatment. By this method, compositional analysis of given oligosaccharides may be accomplished and the presence of $G_{2S}$, $I_{2S}$, I and G containing building blocks assessed. With this information, rapid convergence to a single sequence could be completed by judicious application of the heparinases (regardless of their exact substrate specificity), since cleavage would give mass information on either side of the cleavage site. Thus, in the octasaccharide (example 1) case, application of exhaustive nitrous acid would yield $1\times\Delta UMan_{6S}$, $2\times I_{2S}Man_{6S}$ and $1\times GMan_{6S}$. Then, digestion of this octasaccharide, after tagging, with heparinase III under any conditions (forcing or non-forcing) would result in the formation of a hexasaccharide m/z 5958.7 and a disaccharide, immediately fixing the sequence. A similar sequence of events may be used with heparinase I to converge to a single sequence for the octasaccharide.

While there are caveats to the use of any one particular system for sequence analysis, whether the system is chemical degradation or enzymatic analysis, the sequencing strategy presented here is not critically dependent on any, single technique. One of the major strengths of the sequencing strategy of the invention is the flexibility of our approach and the integration of MALDI and the coding scheme which enable the ability to adapt to different experimental constraints [For example, the recently cloned mammalian heparanase is another possible experimental constraint. M. D. Hulett et al., *Nat. Med.* 5,793 (1999); I. Vlodavsky et. al., *Nat. Med.* 5, 803 (1999).]. As stated additional or different sets of experimental constraints may be used to not only arrive at a unique solution but also may be used to validate or confirm the solution from a given set of experimental constraints.

Example 8

Methods for Identifying Protein-polysaccharide Interactions and Improved Methods for Sequencing To identify HLGAG sequences that bind to a particular protein, the most common methodology involves affinity fractionation of oligosaccharides using a particular HLGAG subset, namely porcine intestinal mucosa heparin. Enzymatically or chemically derived heparin oligosaccharides of a particular length are passed over a column of immobilized protein. After washing, the bound fraction is eluted using high salt to disrupt interactions between the sulfates on the polysaccharide and basic residues on the protein; interactions which are crucial for binding. Eluted oligosaccharides are then characterized, typically by NMR. In this manner, sequences that bind to a number of proteins, including antithrombin III (AT-III), basic fibroblast growth factor (FGF-2), and endostatin have been identified.

While rigorous and well tested, this approach suffers from a number of limitations. First, column chromatography requires large (milligram) amounts of material for successful analysis. Of the entire family of HLGAGs, only heparin is available in these quantities. However, heparin, due to its high sulfate content, contains a limited number of sequences, biasing the selection procedure. Thus, there is no opportunity to sample or select for unusual sequences that might in fact bind with high affinity. In vivo HLGAG-binding proteins sample and bind to the more structurally diverse heparan sulfate (HS) chains of proteoglycans at the cell surface where heparin-like sequences (i.e., sequences with a high degree of sulfation) do not always predominate. Heparin, while structurally related to HS, is present in vivo only in mast cells. For these reasons, heparin is not always an appropriate analog of cell surface HS, and in fact, the exclusive use of heparin in affinity fractionation experiments has created confusion in the field. One example illustrates this point. FGF-2 binds to a specific subset of heparan sulfate sequences that contain a critical 2-O sulfated idurnoate residue. Column chromatography has separated a high affinity binder of FGF-2, the sequence(s) of which have been identified as oligosaccharides containing the predominant trisulfated disaccharide $[I_{2S}H_{NS,6S}]_n$ (n=3–6). However, rigorous examination of the crystal structures of FGF-2, including co-crystals of FGF with HLGAG oligosaccharides, indicates that only three contacts between sulfates and basic residues on FGF-2 are important for high affinity binding.

Using the mass spectrometric approach of the invention we have developed an improved way to identify polysaccharide-protein interactions. The advantage of this approach is that it is highly sensitive, requiring only picomoles of material, which may be isolated from in vivo sources. As described below the approach may be used for the identification and sequencing of oligosaccharides that bind to proteins using picomoles of material. As a proof of concept, we show herein that this novel methodology is functionally equivalent to the established column affinity fractionation method for three proteins: FGF-1, FGF-2 and ATIII, using heparin oligosaccharides as a model system. Furthermore, we show herein that this system can be extended such that heparan sulfate isolated from the cell surface can be used to isolate binding proteins, demonstrating that, for the first time, unbiased, biologically relevant HLGAGs can be used to identify binding sequences.

Methods

Protein preparation and immobilization. ATIII was incubated overnight with excess porcine mucosal heparin, then biotinylated with EZ-link sulfo-NHS biotin (Pierce). Canon NP Type E transparency film was taped to the MALDI sample plate and used as a protein immobilization surface. FGF-1 and FGF-2 were immobilized by spotting 1 $\mu$l of aqueous solution on the film and air-drying. ATIII was immobilized by first drying 4 $\mu$g neutravidin on the film surface, then adding biotinylated ATIII to the neutravidin spot. Heparin was removed by washing ten times with 1M NaCl and ten times with water.

Saccharide binding, selection and analysis. Saccharides were derived from a partial digest of porcine mucosal heparin by heparinase I. The hexasaccharide fraction was obtained by size exclusion chromatography on Biogel P-6 and lyophilized to dryness. Saccharides were bound to immobilized proteins by spotting 1 µl of aqueous solution on the protein spot for at least five minutes. Unbound saccharides were removed by washing with water fifteen times. For selection experiments, the spot was washed ten times with various NaCl concentrations, followed by ten water washes. Caffeic acid matrix in 50% acetonitrile with 2 pmol/µl $(RG)_{19}R$ was added to the spot prior to MALDI analysis. All saccharides were detected as noncovalent complexes with $(RG)_{19}R$ using MALDI parameters described herein.

Saccharide digestion by heparinase I or III. Saccharides selected for FGF-2 binding were digested with heparinases I or III by spotting 8 µg of enzyme in water after selection was completed. The spot was kept wet for the desired digestion time by adding water as necessary. Caffeic acid matrix with 2 pmol/µl $(RG)_{19}R$ was added to the spot for MALDI analysis.

Isolation, Purification, and Selection of FGF binders from SMC heparan sulfate. Bovine aortic smooth muscle cells (SMCS) were grown to confluency. Cells were washed twice with PBS and then 200 nM heparinase III was added for 1 hr. The supernatant was heated to 50° C. for 10 minutes to inactivate heparinase III and filtered. To remove polynucleotide contamination, the samples were treated with DNAse and RNAse at room temperature overnight. Heparan sulfate was isolated by binding to a DEAE filter, washing away unbound material, and elution using 10 mM sodium phosphate 1M NaCl pH 6.0. The material was then concentrated and buffer exchanged into water using a 3,000 MWCO membrane. The retentate was lyophilized and reconstituted in water. 100 nM heparinase II was added and aliquots were taken at 5, 10, 20, and 30 minutes post-addition. 1 µL was spotted on FGF. After drying, the sample was washed, 2 pmol/µl $(RG)_{19}R$ in matrix was added, and the sample was analyzed as outlined above.

Results

Saccharide binding to FGF-2 and FGF-1. As a first step towards the development of a viable MALDI selection procedure, the FGF system using its prototypic members, viz. FGF-1 and FGF-2 was selected. Initial experiments involved the use of a purified polysaccharide (Hexa 1 of Table 12) that is known to bind with high affinity to FGF. With FGF-2, we found that Hexa 1 binds to FGF-2 and were detected, even with a salt wash of 0.5M NaCl, consistent with the known affinity of Hexa 1 for FGF-2. In addition, when an equimolar mixture of Hexa 1 and Hexa 2 (a low affinity binder) were applied to FGF-2 and washed with 0.2M NaCl to eliminate nonspecific binding, only Hexa 1 was observed. Together, these results point to the fact that, under of the conditions of the experiment, immobilized FGF-2 retained the same binding specificity as FGF in solution. Further demonstrating that binding specificity was intact, heat denaturation of FGF resulted in the detection of no saccharide binders.

TABLE 12

| Saccharide | Sequence |
| --- | --- |
| Hexa 1 | (a) ± DDD or (b) DDMan$_{6S}$ |
| Hexa 2 | ± D4 – 7 |
| Penta 1 | |

FGF affinity fractionation of a hexasaccharide mixture derived from the enzymatic depolymerization of heparin was used to enrich for FGF binders. To determine whether specific binders could be selected from a more complex mixture using our methodology, a hexasaccharide fraction derived from incomplete heparinase I digestion of porcine intestinal mucosa heparin was spotted on immobilized FGF. At least five unique structures were detected in the unfractionated hexasaccharide mixture. Upon a salt wash, only two structures, 8- and 9-sulfated hexasaccharides, remained. Importantly, the same results could alternately be achieved by enriching the spot for specific binders and competing off low affinity binders. FGF-1, which has been shown to have similar binding properties as FGF-2, could also select for the octa- and nonasulfated hexasaccharides from a mixture.

Sequencing saccharides on the MALDI surface. The highly sensitive sequencing methodology of the invention was used to test whether we could derive structural information of FGF high affinity binders on target. The octa- and nonasulfated saccharides were subjected to enzymatic and chemical depolymerization. After saccharide selection, the saccharide sample was depolymerized by heparinase I to obtain sequence information. The nonasulfated hexasaccharide was reduced to a single trisulfated disaccharide indicating that this saccharide is a repeat of $[I_{2S}H_{NS,6S}]$. Digestion of the octasulfated hexasaccharide yielded the trisulfated disaccharide and a pentasulfated tetrasaccharide. That this tetrasaccharide contains an unsulfated uronic acid was confirmed by heparinase III cleavage, which resulted in the disappearance of the tetrasaccharide. Confirmation of our sequencing assignments were made by isolating the octa- and nonasulfated hexasaccharides and sequenced using the methods described herein. Thus, the sequence of the nonasulfated hexasaccharide is ±DDD ($\Delta U_{2S}H_{NS,6S}I_{2S}H_{NS,6S}I_{2S}H_{NS,6S}$) and the sequence of the octasulfated hexasaccharide is ±DD–5.

Saccharide Binding to Antithrombin-III. ATIII is heavily glycosylated, therefore we anticipated that it would not bind well to the MALDI plate. As an alternative strategy, avidin was immobilized on the plate and biotinylated AT-III was bound to the avidin. The ATIII biotinylation reaction was carried out in the presence of heparin to protect the protein's binding site for HLGAG oligosaccharides. After washing off the complexed heparin, penta 1, that contains an intact AT-III pentasaccharide binding sequence was used to verify that the protein was immobilized on the surface and was able to bind saccharides. Penta 1 binding to ATIII was observed up to washes of 0.5M NaCl, consistent with it being a strong binder to ATIII.

Furthermore, this binding is also specific. Introduction of a solution of hexa1, hexa 2, and penta 1 to immobilized ATIII followed by a 0.2 M salt wash to remove non-specific binders resulted in signal only for penta 1. Interestingly, there was no signal from hexa 2 that contains a partially intact ATIII binding site, suggesting that, under our selection conditions, only sequences with a full binding site will be selected for.

Selection of FGF-2 Binders in SMC HS. Heparan sulfate at the cell surface of SMCs is known to contain high affinity sites for FGF binding. In an effort to extend our initial studies with highly sulfated heparin, we sought to identify high affinity FGF binders in heparan sulfate proteoglycans at the cell surface of SMCs. To this end, SMCs were treated with either heparinase I or heparinase III and the HLGAGs isolated and purified. Consistent with the known substrate specificity of the enzymes, the composition of released fragments is different. Fragments were then treated with heparinase II to reduce them in size. At certain time points, the digest was spotted on FGF-2 and selection process was accomplished as outlined above. Consistent with our findings with heparin, a single hexasaccharide was identified to be a high affinity binder for FGF-2, namely the nonasulfated hexasaccharide with a sequence ±DDD.

The above-methodology describes an alternative protocol for the selection of saccharide binders to proteins. This methodology has been applied towards the identification of oligosaccharides derived from heparin that bind to two well-established systems, FGF and ATIII. As shown, this procedure produces identical results to the more established methodology of affinity fractionation. For FGF-1 and FGF-2, high affinity binders can be selected out of a pool of similar saccharides. In addition, ATIII, can be selected for high affinity binders over binders that contain only a partial binding site.

This methodology has a number of critical advantages over prior art strategies. First, it is possible to derive sequence information from the bound saccharides directly on a target. Second, and more substantially, the analysis with both FGF and ATIII required only picomoles of material for both the protein and saccharide. Such an advance makes it feasible to use the more biologically relevant HS isolated from the cell surface as substrates, rather than highly sulfated heparin from mast cells. Finally, while the Example demonstrated this technique for the chemically complex and information dense HLGAGs, it is widely applicable towards identifying other polysaccharide-protein interactions.

Example 9

Methods for Identifying Branching and Methods for Sequencing Branched Polysaccharides Increasing evidence exists that glycosylation patterns are highly influenced by the phenotype of the cell. With the onset of disease, it has been noted that there are changes in glycan structure, especially in the degree of branching. For instance, in pathogenic versus normal prion proteins, there is a decrease in levels of glycans with bisecting GlcNAc residues and increased levels of tri- and tetrantennary structures. By judicious application of enzymatic and chemical degradation the identity of branched chains may also be identified.

Figure 8:
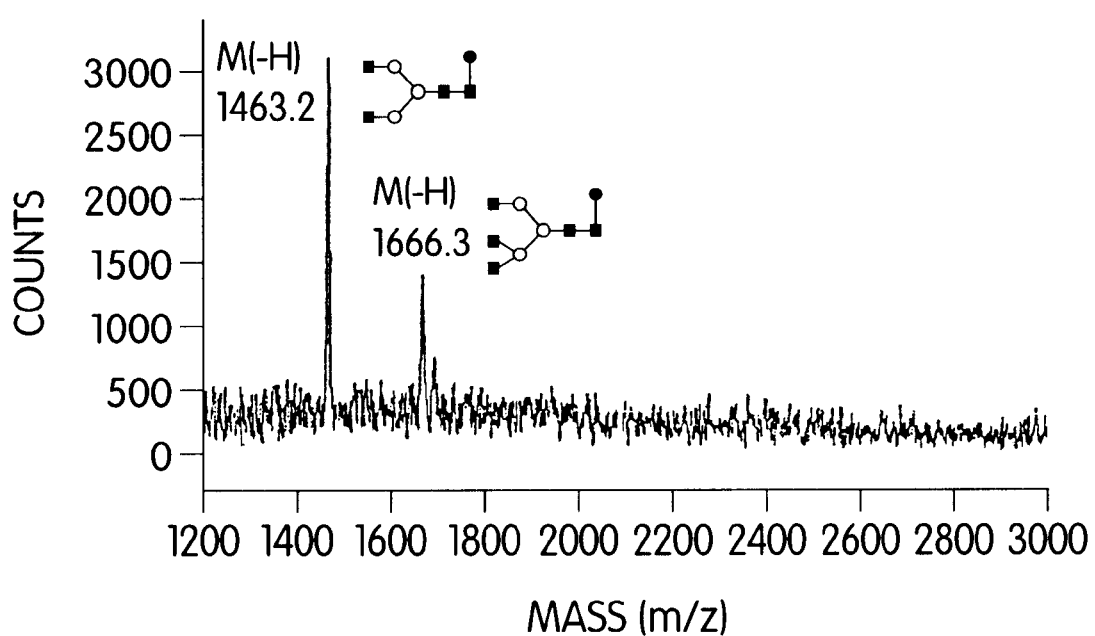
FIG. 8 is a graph depicting MALDI-MS analysis of the extended core structures derived from enzymatic treatment of a mixture of bi- and triantennary structures.

MS Analysis of Complex Glycan Structures: As shown in FIG. 8, the extended core structures generated from complex N-glycan structures were enzymatically generated and identified. MALDI-MS analysis was performed on the extended core structures derived from enzymatic treatment of a mixture of bi- and triantennary structures. 1 pmol of each saccharide was subjected to digest with an enzyme cocktails that included sialidase from *A. urefaciens* and β-galactosidase from *S. pneumonia*. The mass signature of 1462.4 indicates that one of the structures is biantennary with a core fucose moiety, while the mass signature of 1665.8 is indicative of a triantennary structure, also with a core fucose. [○]=mannose; [★]=fucose; [■]=N-acetylglucosamine; [□]=galactose; and [Δ]=N-acetylneuraminic acid.

MALDI-MS sequencing of the N-linked polysaccharide of PSA: Next, rapid sequencing of the glycan structure of PSA from normal prostate tissue was performed (FIG. 9). FIG. 9 is data arising from MALDI-MS microsequencing of the PSA polysaccharide structure. MALDI-MS was completed using 500 fmol of saccharide. Analysis was completed with a saturated aqueous solution of 2,5-dihydroxybenzoic with 300 mM spermine as an additive. Analytes were detected in the negative mode at an accelerating voltage of 22 kV. 1 μL of matrix was added to 0.5 μL of aqueous sample and allowed to dry on the target. (A) MS of the intact polysaccharide structure. Peaks marked with an asterisk are impurities, and the analyte peak is detected both as M-H (m/z 2369.5) and as a monosodiated adduct (M+Na-2H, m/z 2392.6). (B) Treatment of [A] with sialidase from *A. urefaciens*. 10 pmol of saccharide was incubated with enzyme overnight at 37° C. in 10 mM sodium acetate pH 5.5 according to the manufacturer's instructions. Two new saccharides were seen, the first, at m/z 2078 corresponding to the loss of one sialic acid moiety and the second at m/z 1786.9 corresponding to the loss of two sialic acids from the non-reducing end. (C) Digest of [B] with galactosidase from *S. pneumonia*. Digest procedures were completed essentially as described above. A signal product at m/z 1462.8 indicated that two galactose residues were removed upon treatment of [B] with the enzyme. (D) Digest of [C] with N-acetylhexosaminidase from *S. pneumonia*. One product was observed as both M-H (m/z 1056.3) and M+Na-2H (m/z 1078.1) corresponding to the loss of two N-acetylhexosamine units from [C]. A Table of the analysis scheme with schematic structure and theoretical molecular masses is presented in the center of FIG. 9. Shown are the parent polysaccharide and enzymatically derived products seen in this analysis. [○]=mannose; [♀]=fucose; [■]=N-acetylglucosamine; [□]=galactose; and [Δ]=N-acetylneuraminic acid.

Studies of the intact polysaccharide via NMR (large quantities of PSA were required for this study) yielded sequence information of the glycan [Belanger, A., van Halbeek, H., Graves, H. C. B., Grandbois, K., Stamey, T. A., Huang, L., Poppe, I., and Labrie, F., Prostate, 1995. 27: p. 187–197]. Similar to other N-linked glycoproteins, as stated above, PSA contains a core biantennary branched motif. Extending from each mannose arm of PSA is a trisaccharide unit. Together these modifications indicated an expected molecular mass of 2370 Da for the intact polysaccharide. Using MALDI-MS and an exoglycosidase array we have sequenced the putative structure for the N-linked polysaccharide on PSA (FIG. 9). Analysis of the intact polysaccharide yields a molecular mass of 2370 Da (FIG. 9A), identical to the predicted molecular mass based on its structure. In fact for all structures and enzymatic products derived from them, a mass accuracy of less than one Dalton is realized.

Figure 9A:
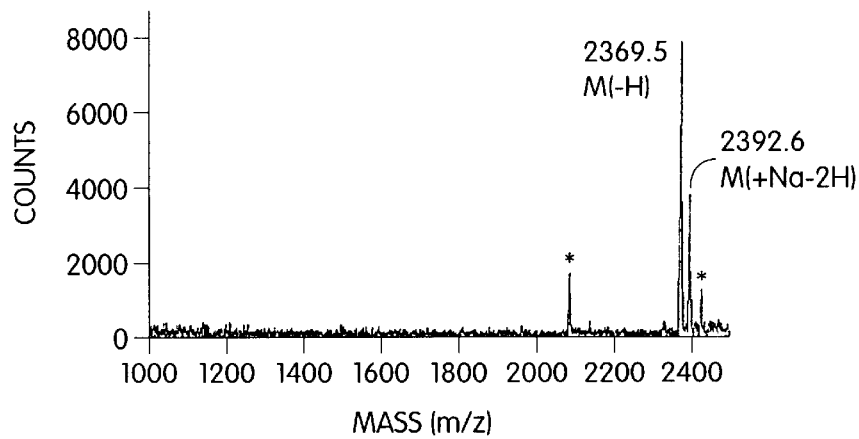
FIG. 9 is a graph depicting MALDI-MS analysis of the PSA polysaccharide. (A) intact polysaccharide structure. (B) Treatment of [A] with sialidase from *A. urefaciens*. (C) Digest of [B] with galactosidase from *S. pneumoniae*. (D) Digest of [C] with N-acetylhexosaminidase from *S. pneumonia*. (E) Table of the analysis scheme with schematic structure and theoretical molecular masses. [○]=mannose; [★]=fucose; [■]=N-acetylglucosamine; [□]=galactose; and [Δ]=N-acetylneuraminic acid. Peaks marked with an asterisk are impurities, and the analyte peak is detected both as M-H (m/z 2369.5) and as a monosodiated adduct (M+Na-2H, m/z 2392.6).
Figure 9B:
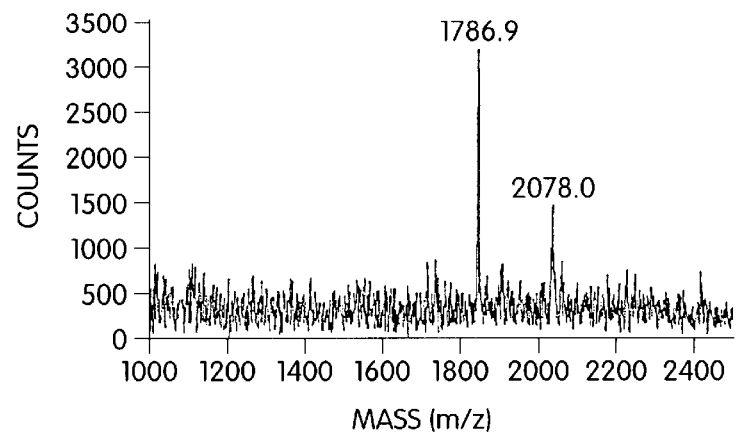
Figure 9C:
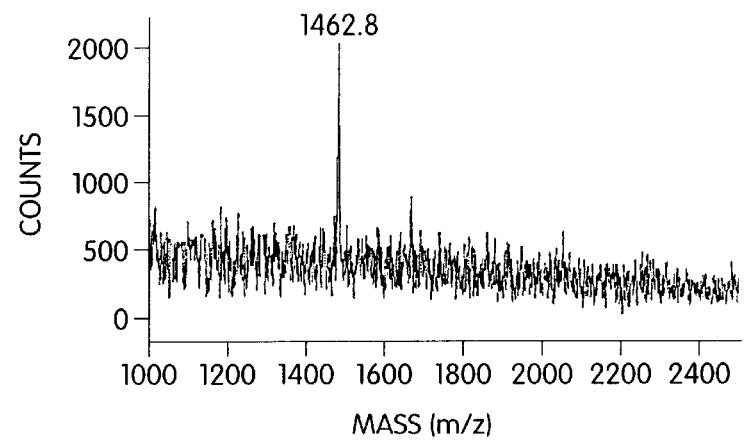
Figure 9D:
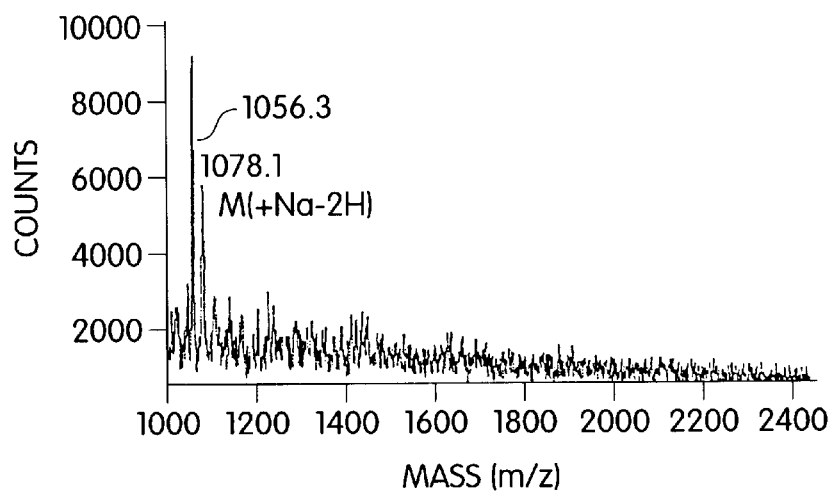
Figure 9E:
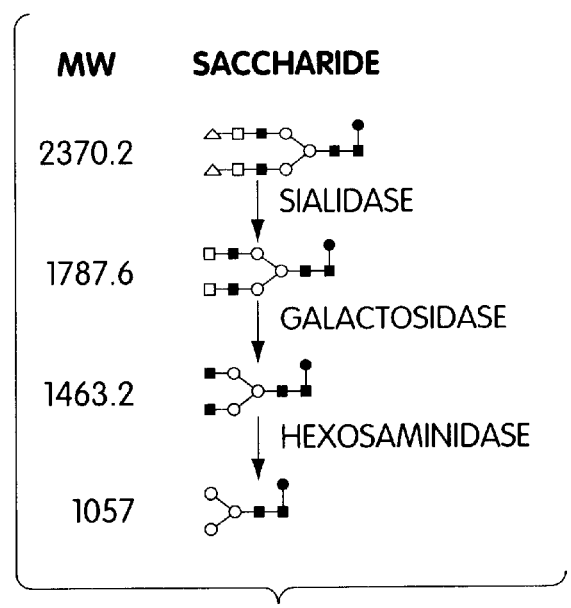

In initial studies, we had found that maximum sensitivity was obtained with 2,5-dihydroxybenzoic acid as the matrix with spermine as an additive [Mechref, Y. and M. V. Novotny, Matrix-assisted laser desorption/ionization mass spectrometry of acidic glycoconjugates facilitated by the use of spermine as a co-matrix. J Am Soc Mass Spectrom, 1998. 9(12): p. 1293–302.]. In this case, oligosaccharides were detected as negative ions. As outlined above, these conditions yielded maximal sensitivity (a limit of detection of around 500 fmol or about 1.5 ng) and also a homogenous signal, which is free of detectable adducts. Of note is the fact that negative mode detection makes amenable the analysis of sialic-containing pendant arms, but detection can also be done in the positive mode with different matrix conditions. Treatment of the polysaccharide with sialidase (specific cleavage of 2Neuα→6,8 linkages) resulted in a mass decrease of 618 Da consistent with the cleavage of two sialic acid residues (FIG. 9B). Treatment of this saccharide with β-galactosidase resulted in a further 360 Da decrease in mass, confirming the presence of two galactose residues located proximate to the sialic acids (FIG. 9C). Importantly when the asilao structure of FIG. 9B was treated with another enzyme besides β-galactosidase, no reduction in mass was observed, confirming the identity of these units as β-linked galactose residues. Via systematic application of the exoglycosidases, we can "read through" the entire sequence of the putative glycan structure of PSA. In addition, not only can we "read through" the structure, but our methodology was able to complete the analysis using submicrogram amounts of material. Also, since at every step of "reading" the sequence we determined the mass, we had an internal control to ensure that our assumptions of enzyme specificity and N-glycan structure were correct.

Direct Sequencing of the PSA Polysaccharide Information about the structure of the sugar moiety of PSA can not only be derived by isolating the sugar and sequencing it (such as by using the above methodology), but we can also derive information about the sugar structure without removal from the protein. FIG. 10 shows the results of sequencing the sugar of PSA (Sigma Chemical). FIG. 10 shows the results of enzymatic degradation of the saccharide chain directly off of PSA. 50 pmol of PSA (~1.4 µg) of PSA was denatured by heat treatment at 80° C. for 20 minutes. Then the sample was sequentially treated with the exoenzymes (B–D). After overnight incubation at 37° C., 1 pmol of the digested PSA was examined by mass spectrometry. Briefly, the aqueous sample was mixed with sinapinic acid in 30% acetonitrile, allowed to dry, and then examined by MALDI TOF. All spectra were calibrated externally with a mixture of myoglobin, ovalbumin, and BSA to ensure accurate molecular mass determination. (A) PSA before the addition of exoenzymes. The measured mass of 28,478 agreed well with the reported value of 28,470. (B) Treatment of (A) with sialidase resulted in a mass decrease of 287 Da, consistent with the loss of one sialic acid residue. (C) Treatment of (B) with galactosidase. A further decrease of 321 Da indicated the loss of two galactose moieties. (D) Upon digestion of (C) with hexosaminidase, a decrease of 393 Da indicated the loss of two N-acetylglucosamine residues.

Figure 10A:
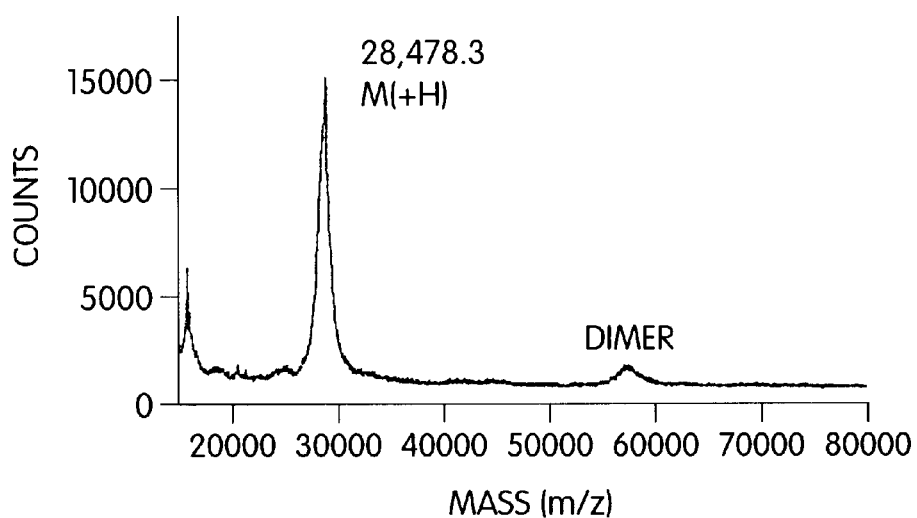
FIG. 10 is a graph depicting the results of enzymatic degradation of the saccharide chain directly off of PSA. (A) PSA before the addition of exoenzymes. (B) Treatment of (A) with sialidase results in a mass decrease of 287 Da, consistent with the loss of one sialic acid residue. (C) Treatment of (B) with galactosidase. (D) Upon digestion of (C) with hexosaminidase, a decrease of 393 Da indicates the loss of two N-acetylglucosamine residues.
Figure 10B:
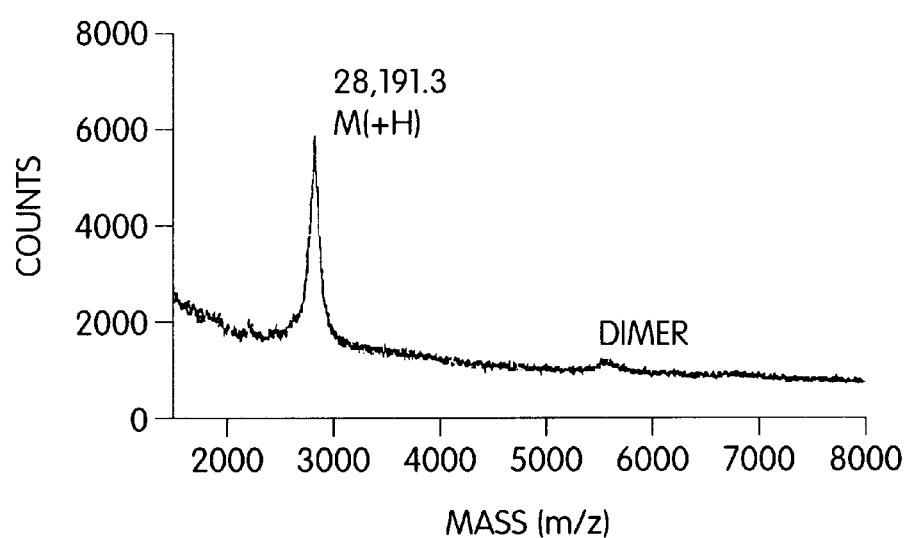
Figure 10C:
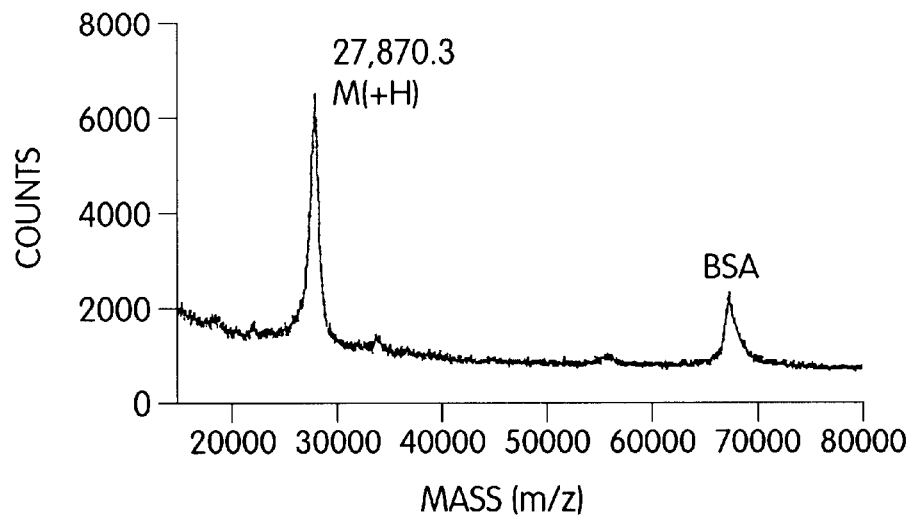
Figure 10D:
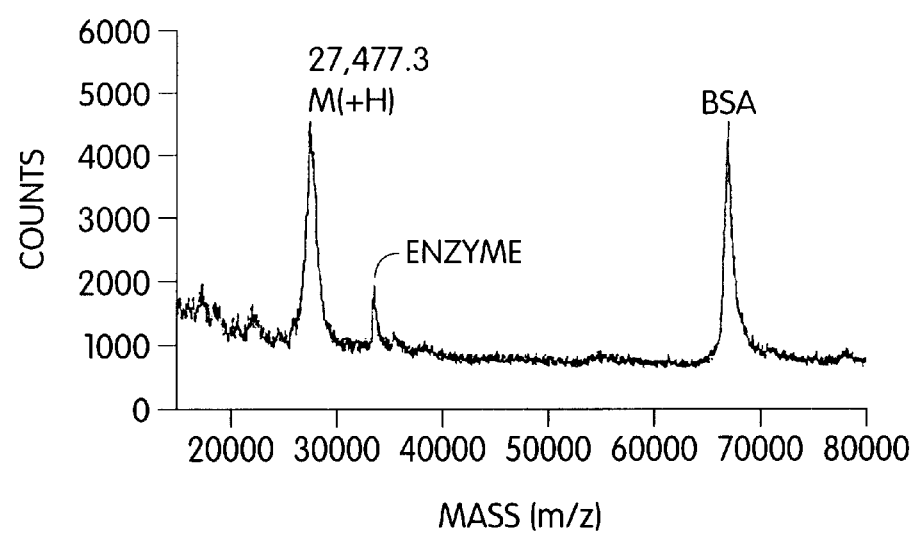

The protein had a measured mass of 28,478.3 (FIG. 10A). Treatment of the intact protein with sialidase resulted in a decrease of 287 Da, consistent with the loss of one sialic acid residue (FIG. 10B). Additional treatment with galactosidase resulted in a decrease in mass of 321, consistent with the loss of two galactose residues (FIG. 10C). Finally, treatment with N acetylhexosaminidase resulted in cleavage of two GlcNAc moieties (FIG. 10D).

Figure 11A:
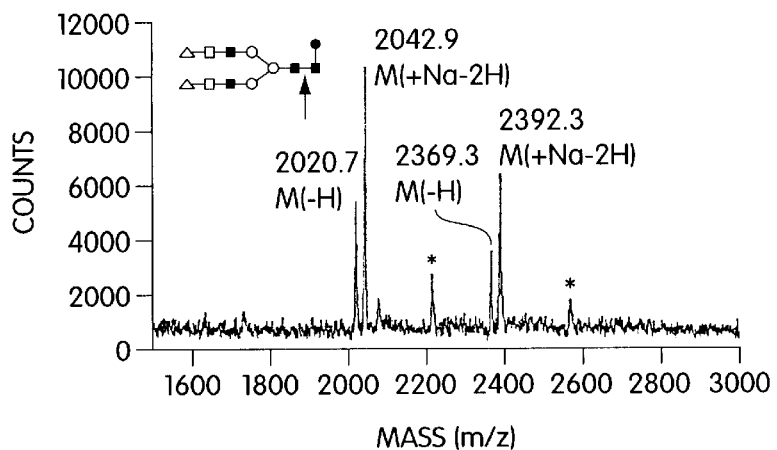
FIG. 11 is a graph depicting the results of treatment of biantennary and triantennary saccharides with endoglycanse F2. (A) Treatment of the biantennary saccharide results in a mass decrease of 348.6, indicating cleavage between the GlcNAc residues. (B) Treatment of the triantennary saccharide with the same substituents results in no cleavage showing that EndoF2 primarily cleaves biantennary structures. (C) EndoF2 treatment of heat denatured PSA. There is a mass reduction of 1709.7 Da in the molecular mass of PSA (compare B4C and B3a) indicating that the normal glycan structure of PSA is biantennary.
Figure 11B:
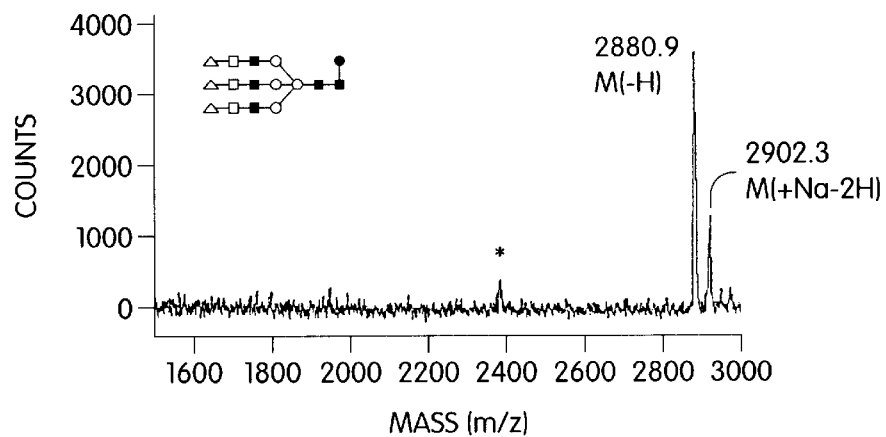
Figure 11C:
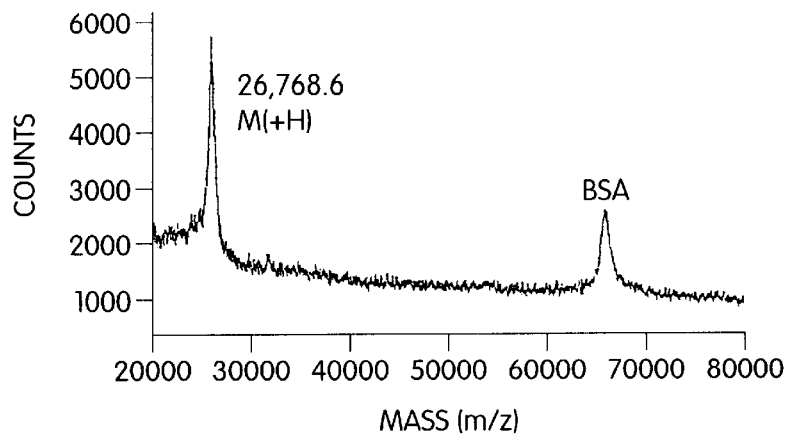

Glycotyping of PSA by EndoF2 Treatment EndoF2 is an endoglycanase that clips only biantennary structures. Tri- and tetrantennary structures do not serve as substrates for this enzyme (FIG. 11). In this way, EndoF2 treatment of a glycan structure, either attached to the protein or after isolation, was used to identify branching identity. This becomes especially important in light of the fact that aberrant changes in glycosylation patterns usually result in increased branching. In addition, EndoF2 was used to cleave glycan structures that were still attached to the protein of interest. Indeed, treatment of PSA with EndoF2 resulted in mass shift, consistent with the loss of a biantennary, complex type glycan structure. FIG. 11 showed the results of treatment of biantennary and triantennary saccharides with endoglycanse F2. (A) Treatment of the biantennary saccharide resulted in a mass decrease of 348.6, indicating cleavage between the GIcNAc residues. (B) Treatment of the triantennary saccharide with the same substituents resulted in no cleavage showing that EndoF2 primarily cleaves biantennary structures. (C) EndoF2 treatment of heat denatured PSA. There was a mass reduction of 1709.7 Da in the molecular mass of PSA (compare 11C and 11A) indicating that the normal glycan structure of PSA was biantennary.

A computer system for implementing the system 100 of FIG. 1 as a computer program typically includes a main unit connected to both an output device which displays information to a user and an input device which receives input from a user. The main unit generally includes a processor connected to a memory system via an interconnection mechanism. The input device and output device also are connected to the processor and memory system via the interconnection mechanism.

It should be understood that one or more output devices may be connected to the computer system. Example output devices include a cathode ray tube (CRT) display, liquid crystal displays (LCD), printers, communication devices such as a modem, and audio output. It should also be understood that one or more input devices may be connected to the computer system. Example input devices include a keyboard, keypad, track ball, mouse, pen and tablet, communication device, and data input devices such as sensors. It should be understood the invention is not limited to the particular input or output devices used in combination with the computer system or to those described herein.

The computer system may be a general purpose computer system which is programmable using a computer programming language, such as C++, Java, or other language, such as a scripting language or assembly language. The computer system may also include specially programmed, special purpose hardware. In a general purpose computer system, the processor is typically a commercially available processor, of which the series x86, Celeron, and Pentium processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which Windows NT, Linux, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, known as a floppy disk, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the invention is not limited thereto. It should also be understood that the invention is not limited to a particular memory system.

The invention is not limited to a particular computer platform, particular processor, or particular high-level programming language. Additionally, the computer system may be a multiprocessor computer system or may include multiple computers connected over a computer network. That each module (e.g. 108, 112) in FIG. 1 may be separate modules of a computer program, or may be separate computer programs. Such modules may be operable on separate computers. Data (e.g. 102, 110, 114, 116, and 118) may be stored in a memory system or transmitted between computer systems. The invention is not limited to any particular implementation using software or hardware or firmware, or any combination thereof. The various elements of the system, either individually or in combination, may be implemented as a computer program product tangibly embodied in a machine-readable storage device for execution by a computer processor. Various steps of the process may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

The present invention is not to be limited in scope by examples provided, since the examples are intended as a single illustration of one aspect of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. All references, patents and patent publications that are recited in this application are incorporated in their entirety herein by reference.

We claim:

1. A method for identifying a polysaccharide-protein interaction, comprising:
   contacting a protein-coated MALDI surface with a polysaccharide containing sample to produce a polysaccharide-protein-coated MALDI surface,
   removing unbound polysaccharide from the polysaccharide-protein-coated MALDI surface, and
   performing MALDI mass spectrometry to identify the polysaccharide that specifically interacts with the protein coated on the MALDI surface.

2. The method of claim 1, wherein a MALDI matrix is added to the polysaccharide-protein-coated MALDI surface.

3. The method of claim 1, further comprising applying an experimental constraint to the polysaccharide bound on the polysaccharide-protein-coated MALDI surface before performing the MALDI mass spectrometry analysis.

4. The method of claim 3, wherein the experimental constraint applied to the polymer is digestion with an exoenzyme.

5. The method of claim 3, wherein the experimental constraint applied to the polymer is digestion with an endoenzyme.

6. The method of claim 3, wherein the experimental constraint applied to the polymer is selected from the group consisting of restriction endonuclease digestion; chemical digestion; chemical modification; and enzymatic modification.

7. The method of claim 1, wherein the polysaccharide is a heparin-like-glycosaminoglycan.

8. The method of claim 3, wherein the experimental constraint is selected from the group consisting of enzymatic digestion, interaction with a binding compound, and chemical peeling.

9. The method of claim 6, wherein the enzymatic modification is sulfation.

* * * * *